United States Patent [19]
Howard, Jr. et al.

[11] Patent Number: 6,166,020
[45] Date of Patent: Dec. 26, 2000

[54] ARYL AND HETEROARYL ALKOXYNAPHTHALENE DERIVATIVES

[75] Inventors: Harry R. Howard, Jr., Bristol; Bertrand L. Chenard, Waterford, both of Conn.; John E. Macor, Penfield, N.Y.; Kevin D. Shenk, Groton; Kishor A. Desai, Ledyard, both of Conn.

[73] Assignee: Pfizer Inc., New York, N.Y.

[21] Appl. No.: 09/295,138

[22] Filed: Apr. 20, 1999

Related U.S. Application Data

[63] Continuation of application No. 08/765,014, filed as application No. PCT/IB95/00381, May 18, 1995, abandoned, which is a continuation-in-part of application No. 08/268,376, Jun. 29, 1994, abandoned, and a continuation-in-part of application No. 08/306,089, Sep. 14, 1994, abandoned, and a continuation-in-part of application No. 08/308,320, Sep. 19, 1994, abandoned.

[51] Int. Cl.$^7$ .................... A61K 31/496; C07D 403/12; C07D 487/04

[52] U.S. Cl. ................. 514/253.04; 514/254.06; 544/362; 544/366; 544/370; 544/238; 544/295; 544/357; 544/360; 544/363; 544/367; 544/369; 544/373; 544/379; 544/392; 544/394; 544/395

[58] Field of Search ..................... 544/238, 295, 544/357, 360, 362, 363, 367, 369, 370, 373, 377, 379, 392, 394, 366; 514/252, 253, 255, 253.04, 254.06

[56] References Cited

U.S. PATENT DOCUMENTS 5,143,916  9/1992  Lavielle et al. .................... 514/255

FOREIGN PATENT DOCUMENTS 434561  6/1991  European Pat. Off. .
94/21619 9/1994  WIPO .

OTHER PUBLICATIONS

Millan et al, *Journal of Pharmacology and Experimental Therapeutics,* 262, pp. 451–463, 1992.
Chavloff et al, *Journal of Pharmacology and Experimental Therapeutics,* 243, pp. 1159–1166, 1987.
G Lennon et al, *Drug Dev. Res* 22 pp. 25–36, 1991.
S Axena, *Pharmac. Ther.* vol. 66, pp. 339–368, 1995.
Rasmussen et al, in *Annual Reports in Medicinal Chemistry,* pp. 1–9 (1995).

*Primary Examiner*—Emily Bernhardt
*Attorney, Agent, or Firm*—Dr. Peter C. Richardson; Dr. Paul H. Ginsburg; Israel Nissenbaum

[57] ABSTRACT

Compounds of the formula

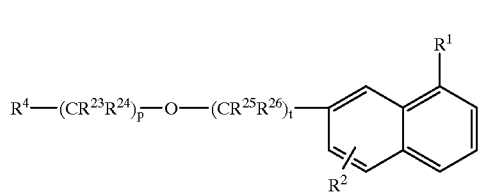

wherein $R^1$, $R^2$, $R^4$, $R^{23}$, $R^{24}$, $R^{25}$ and $R^{26}$ are defined as in the specification.

These compounds are useful psychotherapeutics and are potent serotonin (5-HT$_1$) agonists and antagonists.

3 Claims, No Drawings

ARYL AND HETEROARYL ALKOXYNAPHTHALENE DERIVATIVES

This is a continuation of U.S. Ser. No. 08/765,014, filed Aug. 18, 1997, abandoned, which was the U.S. National filing of International Patent Application No. PCT/IB95/00381, filed May 18, 1995 which was a continuation-in-part of U.S. application Ser. No. 08/268,376, filed Jun. 29, 1994 and a continuation-in-part of U.S. application Ser. No. 08/306,089, filed Sep. 14, 1994 and a continuation-in-part of U.S. application Ser. No. 08/308,320, filed Sep. 19, 1994, all now abandoned.

BACKGROUND OF THE INVENTION

The present invention relates to aryl and heteroaryl alkoxylnaphthalene derivatives, to processes and intermediates for their preparation, to pharmaceutical compositions containing them and to their medicinal use. The compounds of the present invention are selective agonists and antagonists of serotonin 1 (5-$HT_1$) receptors. They are useful in treating or preventing migraine, depression and other disorders for which a 5-$HT_1$ agonist or antagonist is indicated.

European Patent Publication 434,561, published on Jun. 26, 1991, refers to 7-alkyl, alkoxy, and hydroxy substituted-1-(4-substituted-1-piperazinyl)-naphthalenes. The compounds are referred to as 5-$HT_1$ agonists and antagonists useful for the treatment of migraine, depression, anxiety, schizophrenia, stress and pain.

European Patent Publication 343,050, published on Nov. 23, 1989, refers to 7-unsubstituted, halogenated, and methoxy substituted-1-(4-substituted-1-piperazinyl)-naphthalenes as useful 5-$HT_{1A}$ ligand therapeutics.

Glennon et al., refers to 7-methoxy-1-(1-piperazinyl)-naphthalene as a useful 5-$HT_1$ ligand in their article "5-$HT_{1D}$ Serotonin Receptors", Clinical Drug Res. Dev., 22, 25–36 (1991).

Glennon's article "Serotonin Receptors: Clinical Implications", Neuroscience and Behavoral Reviews, 14, 35–47 (1990), refers to the pharmacological effects associated with serotonin receptors including appetite suppression, theromoregulation, cardiovascular/hypotensive effects, sleep, psychosis, anxiety, depression, nausea, emesis, Alzheimers disease, Parkinsons disease and Huntingtons disease.

Ligands with high affinity for the 5-$HT_1$ receptors are well recognized as having therapeutic value for the treatment of human conditions caused by serotonin imbalance.

SUMMARY OF THE INVENTION

The present invention relates to compounds of the formula

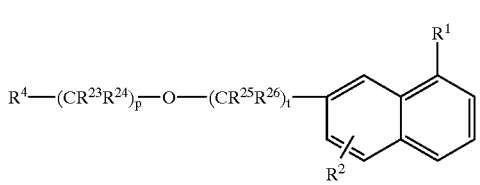

I wherein $R^1$ is

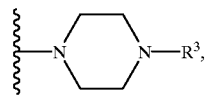

II

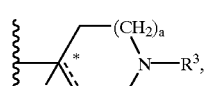

III

IV

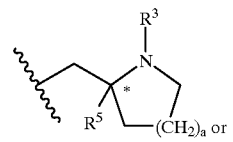

V wherein the broken line in III and V is an optional double bond, and wherein $R^5$ is absent when the broken line is a double bond;

a is 0, 1 or 2;

e is 0, 1 or 2;

m is an integer from zero to six;

n is an integer from one to three;

p is an integer from one to six;

t is an integer from zero to three;

$R^2$ is a substituent on any of the carbon atoms of the naphthalene ring capable of forming an additional bond and each occurence of $R^2$ is independently selected from the group consisting of hydrogen, fluoro, chloro, bromo, iodo, —CN, —$NO_2$, ($C_1$–$C_6$)alkyl optionally substituted with from one to seven fluorine atoms (preferably one to three fluorine atoms), ($C_1$–$C_6$)alkoxy optionally substituted with from one to seven fluorine atoms (preferably one to three fluorine atoms), —($C_1$–$C_5$)thioalkyl optionally substituted with from one to seven fluorine atoms (preferably one to three fluorine atoms), —OH, —$NR^{20}R^{21}$, —$CONR^{20}R^{21}$, and —$CO_2R^{20}$;

$R^3$ is hydrogen, ($C_1$–$C_{10}$)alkyl optionally substituted with from one to seven fluorine atoms (preferably one to three fluorine atoms), —$(CH_2)_m$-aryl, —$(CH_2)_m$—($C_5$–$C_7$)cycloalkyl, —$(CH_2)_n$—$R^{27}$, —$CO_2R^{20}$ or ($C_1$–$C_6$)alkoxy optionally substituted with one to seven fluorine atoms (preferably one to three fluorine atoms); wherein said aryl moeity of said —$(CH_2)_m$-aryl group may optionally be substituted with from one to three substituents independently selected from any of the substituents listed for $R^2$; and wherein said ($C_5$–$C_7$) cycloalkyl moiety of said —$(CH_2)_m$—($C_5$—$C_7$) cycloalkyl group may optionally be substituted with from one to three substituents independently selected from any of the substituents listed for $R^2$;

$R^4$ is

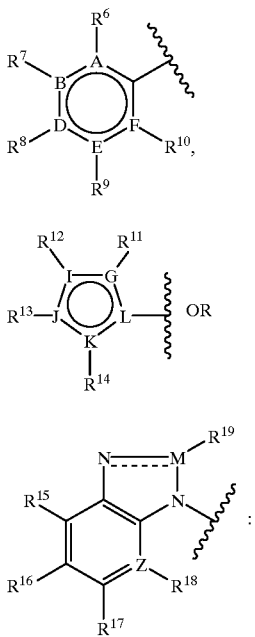

$R^5$ is hydrogen, $(C_1-C_6)$alkyl optionally substituted with from one to seven fluorine atoms (preferably one to three fluorine atoms), —OH, or $(C_1-C_6)$alkoxy optionally substituted with from one to seven fluorine atoms (preferably one to three fluorine atoms); wherein said $(C_1-C_6)$alkyl group may also optionally contain one to three double or triple bonds;

$R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ are each independently selected from hydrogen, bromo, chloro, fluoro, aryl, $(C_1-C_6)$alkyl optionally substituted with from one to seven fluorine atoms (preferably one to three fluorine atoms), $(C_1-C_5)$alkoxy optionally substituted with from one to seven fluorine atoms (preferably one to three fluorine atoms), $(C_1-C_5)$ alkylthio optionally substituted with from one to seven fluorine atoms (preferably one to three fluorine atoms), formyl, —C(=O)$R^{20}$, —CN, —O$R^{20}$, —N$R^{20}R^{21}$, —N$R^{20}SO_2R^{22}$, —N$R^{20}CO_2R^{22}$, —N=C—N(CH$_3$)$_2$, —S(O)$_eR^{26}$, —SO$_2$N$R^{20}R^{21}$, —NO$_2$, aryl, $(C_1-C_6)$ alkylaryl, —(C=O)O$R^{20}$, —(C=O)N$R^{20}R^{21}$, $(C_1-C_6)$alkyl, $(C_1-C_6)$alkenyl, and $(C_1-C_6)$alkynyl;

$R^6$ and $R^7$, $R^7$ and $R^8$, $R^8$ and $R^9$, $R^9$ and $R^{10}$, $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may optionally be taken together to form a five-to-seven-membered alkyl ring, a six-membered aryl ring, a five to seven membered heteroalkyl ring having one heteroatom of N, O, or S, or a five-to six-membered heteroaryl ring having 1 or 2 heteroatoms of N, O, or S;

$R^{19}$ is hydrogen or $(C_1-C_3)$alkyl;

each occurence of $R^{20}$ and each occurence of $R^{21}$ is independently hydrogen, $(C_1-C_6)$alkyl, aryl, or $(C_1-C_6)$alkyl-aryl, or any occurence of $R^{20}$ and $R^{21}$, when attached to the same nitrogen atom, may form, together with the nitrogen to which they are attached, a $(C_4-C_7)$alkyl ring;

$R^{22}$ is $(C_1-C_6)$alkyl, aryl, or $(C_1-C_6)$alkylaryl;

A, B, D, E, and F are each independently C, N, or (C=O);

G, I, J, and K are each independently C, N, O, S, or (C=O), with the proviso that there is at most one of O, (C=O), or S per ring;

L and Z are each independently C or N, wherein $R^{18}$ is absent when Z is N;

M is C, N, or (C—O), wherein $R^{19}$ is absent when M is C=O;

$R^{23}$ and $R^{24}$ are independently selected from hydrogen, —$(C_1-C_6)$alkyl optionally substituted with from one to seven fluorine atoms, preferably one to three fluorine atoms, and when p is greater than 1 then each $R^{23}$ and $R^{24}$ is independently selected from any other $R^{23}$ or $R^{24}$;

$R^{25}$ and $R^{26}$ are independently selected from hydrogen, —$(C_1-C_6)$alkyl optionally substituted with from one to seven fluorine atoms, preferably one to three fluorine atoms, and when t is greater than 1 then each $R^{25}$ and $R^{26}$ is independently selected from any other $R^{25}$ or $R^{26}$;

$R^{27}$ is O$R^{20}$, —C(=O)N$R^{20}R^{21}$, —C(=O)O$R^{20}$, CN, —N$R^{20}$C(=O)$R^{21}$, —O(C=O)$R^{20}$;

a broken line indicates the optional presence of a double bond; and the above aryl groups and the aryl moieties of the above alkylaryl groups are independently selected from phenyl, naphthyl, substituted naphthyl and substituted phenyl, wherein said substituted naphthyl and substituted phenyl may be substituted with one to three groups independently selected from $(C_1$ to $C_4)$alkyl optionally substituted with one to three fluorine atoms, halogen, hydroxy, cyano, carboxamido, nitro, and $(C_1$ to $C_4)$alkoxy optionally substituted with one to three fluorine atoms;

and the pharmaceutically acceptable salts thereof.

The present invention also relates to the pharmaceutically acceptable acid addition salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3-naphthoate)]salts.

The invention also relates to base addition salts of formula I. The chemical bases that may be used as reagents to prepare pharmaceutically acceptable base salts of those compounds of formula I that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(methylglucamine), and the lower alkanolammonium and other base salts of pharmaceutically acceptable organic amines.

The above ring systems described as $R^4$ include but are not limited to pyrrolyl, furyl, thienyl, oxazolyl, isoxazolyl, imidazolyl, thiazolyl, isothiazolyl, pyrazolyl, triazolyl, tetrazolyl, 1,3,5-oxadiazolyl, 1,2,4-oxadiazolyl, 1,3,5-thiadiazolyl, 1,2,4-thiadiazolyl, pyridyl, pyrazinyl, pyrimidinyl, pyridazinyl, 1,2,4-triazinyl, 1,2,3-triazinyl, 1,3, 5-triazinyl, 1,2,5-thiadiazinyl, 1,2,5-oxathiazinyl, 1,2,6-oxathiazinyl, benzoxazolyl, benzothiazolyl, benzisothiazolyl, benzisoxazolyl, benzimidazolyl, thianaphthenyl, isothianaphthenyl, benzofuranyl, isobenzofuranyl, chromenyl, isoindolyl, indolyl, indazolyl, isoquinolyl, quinolyl, phthalazinyl, quinoxalinyl, quinazolinyl, cinnolinyl and benzoxazinyl.

Preferably, only two of the substituents $R^6$, $R^7$, $R^8$, $R^9$, $R^{10}$, $R^{11}$, $R^{12}$, $R^{13}$, $R^{14}$, $R^{15}$, $R^{16}$, $R^{17}$ and $R^{18}$ may optionally be taken together to form a five-to-seven-membered alkyl ring, a six-membered aryl ring, a five to seven membered heteroalkyl ring having one heteroatom of N, O, or S, or a five-to six-membered heteroaryl ring having 1 or 2 heteroatoms of N, O, or S;

The compounds of the invention include all stereoisomers and all optical isomers of the formula I (e.g., R and S enantiomers) and their racemic and diastereomeric mixtures. When $R^1$ is a group of the formula III, IV or V

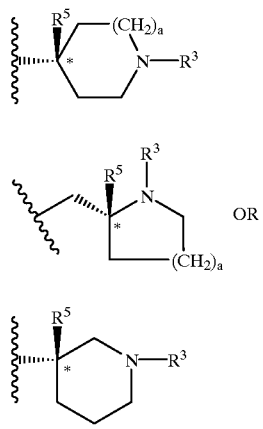

the R enantiomers (e.g., IIIa', IVa' and Va') at the chiral carbon designated by an asterisk in the ring in which "$R^1$" occurs are preferred.

Unless otherwise indicated, the alkyl and alkenyl groups referred to herein, as well as the alkyl moieties of other groups referred to herein (e.g., alkoxy), may be linear or branched, and they may also be cyclic (e.g., cyclopropyl, cyclobutyl, cyclopentyl, or cyclohexyl) or be linear or branched and contain cyclic moieties. Unless otherwise indicated, halogen includes fluorine, chlorine, bromine, and iodine.

Preferred compounds of formula I include the following:

1-{7-[5-(2-methoxyphenyl)-[1,2,4]oxadiazol-3-ylmethoxy]-naphthalen-1-yl}-4-methylpiperazine dihydrochloride hydrate;

1-[7-(5-tert-butyl-[1,2,4]oxadiazol-3-ylmethoxy)-naphthalen-1-yl]-4-methylpiperazine hydrochloride dihydrate;

1-methyl-4-[7-(3-phenyl-[1,2,4]oxadiazol-5-ylmethoxy)-naphthalen-1-yl]-piperazine dihydrochloride hemihydrate;

1-methyl-4-[7-(5-phenyl-[1,2,4]oxadiazol-3-ylmethoxy)-naphthalen-1-yl]-piperazine;

1-{7-[5-(3-methoxyphenyl)-[1,2,4]oxadiazol-3-ylmethoxy]-naphthalen-1-yl}-4-methylpiperazine dihydrochloride hydrate;

1-{7-[5-(3,5-dimethylisoxazol-4-yl)-[1,2,4]oxadiazol-3-ylmethoxy]-naphthalen-1-yl}-4-methylpiperazine dihydrochloride hydrate;

1-{7-[3-(4-methoxyphenyl)-[1,2,4]oxadiazol-5-ylmethoxy)-naphthalen-1-yl}-4-methylpiperazine dihydrochloride hemihydrate;

2-{8-(1-methylpiperidin-4-yl)-naphthalen-2-yloxy]-pyrimidine;

1-methyl-4-[7-(3-phenyl-[1,2,4]oxadiazol-5-ylmethoxy)-naphthalen-1-yl]-piperidine; and 4-{7-[5-(3,5-dimethylisoxazol-4-yl)-[1,2,4]oxadiazol-3-ylmethoxy]-naphthalen-1-yl}-1-methylpiperidine.

Other compounds of formula I include the following:

2-[8-(4-methylpiperazin-1-yl)-naphthalen-2-yloxymethyl]-quinoline;

1-methyl-4-[7-(pyridin-2-ylmethoxy)-naphthalen-1-yl]-piperazine;

1-[7-(5-chlorothiophen-2-ylmethoxy)-naphthalen-1-yl]-4-methylpiperazine;

1-[7-[2-(4-chlorophenyl)-thiazol-4-ylmethoxy]-naphthalen-1-yl]-4-methylpiperazine;

1-methyl-4-[7-(3-pyridin-3-ylpropoxy)-naphthalen-1-yl]-piperazine;

6-chloro-5-[2-[8-(4-methylpiperazin-1-yl)-naphthalen-2-yloxy]-ethyl]-1,3-dihydroindol-2-one;

1-[7-(6-fluoro-4H-benzo[1,3-dioxin-8-ylmethoxy)-naphthalen-1-yl]-4-methylpiperazine;

1-[7-(5,6-dichloropyridin-2-ylmethoxy)-naphthalen-1-yl]-4-methylpiperazine;

7-chloro-2-[8-(4-methylpiperazin-1-yl)-naphthalen-2-yloxymethyl]-quinoline;

1-[7-(2-methoxy-5-pyridin-2-yl-benzyloxy)-naphthalen-1-yl]-piperazine; and 1-methyl-4-[7-(1-phenyl-1H-tetrazol-5-yloxy)-naphthalen-1-yl]-piperazine dihydrochloride;

1-methyl-4-{7-[5-(3-trifluoromethylphenyl)-[1,2,4]oxadiazol-3-ylmethoxy]-naphthalen-1-yl}-piperazine dihydrochloride;

1-{7-[5-(4-methoxyphenyl)-[1,2,4]oxadiazol-3-ylmethoxy]-naphthalen-1-yl}-4-methylpiperazine dihydrochloride hydrate;

1-{7-[5-(4-chlorophenyl)-[1,2,4]oxadiazol-3-ylmethoxy]-naphthalen-1-yl}-4-methylpiperazine dihydrochloride dihydrate;

1-{7-[5-(2,4-dichlorobenzyl)-[1,2,4]oxadiazol-3-ylmethoxy]-naphthalen-1-yl}-4-methylpiperazine dihydrochloride hydrate;

1-{7-[3-(4-chlorobenzyl)-[1,2,4]oxadiazol-5-ylmethoxy]-naphthalen-1-yl}-4-methylpiperazine dihydrochloride hemihydrate;

5-chloro-2-[8-(4-methylpiperazin-1-yl)-naphthalen-2-yloxymethyl]-benzooxazole dihydrochloride hydrate;

2-[8-(4-methylpiperazin-1-yl)-naphthalen-2-yloxymethyl]-5-trifluoromethylbenzothiazole dihydrochloride dihydrate;

1-{7-[3-(2-methoxyphenyl)-[1,2,4]oxadiazol-5-ylmethoxy]-naphthalen-1-yl}-4-methylpiperazine dihydrochloride hydrate;

1-{7-[3-(4-chlorophenyl)-[1,2,4]oxadiazol-5-ylmethoxy]-naphthalen-1-yl}-4-methylpiperazine dihydrochloride;

1-{7-[5-(2-methoxyphenyl)-[1,2,4]oxadiazol-3-ylmethoxymethyl]-naphthalen-1-yl}-4-methylpiperazine dihydrochloride hydrate;

1-(7-{1-[5-(4-chlorophenyl)-[1,3,4]oxadiazol-2-yl]ethoxy}-naphthalen-1-yl)-4-methylpiperazine hydrochloride dihydrate;

1-{7-[3-(2-fluorophenyl)-[1,2,4]oxadiazol-5-ylmethoxy]-naphthalen-1-yl}-4-methylpiperazine dihydrochloride;

5-bromo-2-[8-(4-methylpiperazin-1-yl)-naphthalen-2-yloxymethyl]-benzooxazole dihydrochloride;

6-fluoro-2-[8-(4-methylpiperazin-1-yl)-naphthalen-2-yloxymethyl]-benzooxazole dihydrochloride;

6-methoxy-2-[8-(4-methylpiperazin-1-yl)-naphthalen-2-yloxymethyl]-benzothiazole dihydrochloride;

2-[8-(4-methylpiperazin-1-yl)-naphthalen-2-yloxy]-pyrimidine;
2-[8-(4-methylpiperazin-1-yl)-naphthalen-2-yloxy]-5-trifluoromethyl-pyrimidine;
5-fluoro-2-[8-(4-methylpiperazin-1-yl)-naphthalen-2-yloxy]-pyrimidine;
1-[7-(5-chloropyridin-2-yloxy)-naphthalen-1-yl]-4-methyl-piperazine;
2-[8-(4-methylpiperazin-1-yl)-naphthalen-2-yloxy]-nicotinonitrile;
2-[8-(4-methylpiperazin-1-yl)-naphthalen-2-yloxymethyl]-quinoline;
3-[8-(4-methylpiperazin-1-yl)-naphthalen-2-yloxy]-6-phenylpyridazine;
1-methyl-4-[7-(4-phenyl-thiophen-2-ylmethoxy)-naphthalen-1-yl]-piperazine;
1-{7-[5-(4-chloro-phenyl)-thiophen-3-ylmethoxy]-naphthalen-1-yl}-4-methylpiperazine;
1-[7-(2-methoxy-6-phenyl-pyridin-4-ylmethoxy)-naphthalen-1-yl]-4-methylpiperazine;
1-methyl-4-[7-(2-methyl-6-phenyl-pyridin-4-ylmethoxy)-naphthalen-1-yl]-piperazine;
1-{7-[2-(2,6-dimethyl-pyridin-4-yl)-ethoxy]-naphthalen-1-yl}-4-methyl-piperazine;
1-methyl-4-[7-(6-phenyl-pyridin-2-ylmethoxy)-naphthalen-1-yl]-piperazine;
1-methyl-4-[7-(2-pyridin-2-yl-ethoxy)-naphthalen-1-yl]-piperazine;
1-methyl-4-{7-[3-(6-methyl-pyridin-2-yl)-propoxy]-naphthalen-1-yl}-piperazine;
2-[8-(4-methyl-piperazin-1-yl)-naphthalen-2-yloxymethyl]-4-phenyl-pyrimidine;
5-fluoro-2-[8-(4-methyl-piperazin-1-yl)-naphthalen-2-yloxymethyl]-pyrimidine;
4,6-dimethyl-2-[8-(4-methyl-piperazin-1-yl)-naphthalen-2-yloxymethyl]-pyrimidine;
4-[8-(4-methyl-piperazin-1-yl)-naphthalen-2-yloxymethyl]-2-phenyl-pyrimidine;
1-methyl-4-[7-(5-phenyl-thiophen-3-ylmethoxy)-naphthalen-1-yl]-piperazine;
2-[8-(1-methyl-piperidin-4-yl)-naphthalen-2-yloxymethyl]-6-phenyl-pyrazine;
2,4-dimethyl-6-[8-(4-methyl-piperazin-1-yl)-naphthalen-2-yloxymethyl]-pyrimidine;
2-methyl-4-{2-[8-(4-methyl-piperazin-1-yl)-naphthalen-2-yloxy]-ethyl}-pyrimidine;
2-[8-(4-methyl-piperazin-1-yl)-naphthalen-2-yloxymethyl]-6-phenyl-pyrazine;
2,3-dimethyl-5-[8-(4-methyl-piperazin-1-yl)-naphthalen-2-yloxymethyl]-pyrazine;
5-(4-chloro-phenyl)-3-[8-(4-methyl-piperazin-1-yl)-naphthalen-2-yloxymethyl]-pyridazine;
4-(4-chloro-phenyl)-3-methyl-6-[8-(1-methyl-piperidin-4-yl)-naphthalen-2-yloxymethyl]-pyridazine;
5-[8-(4-methyl-piperazin-1-yl)-naphthalen-2-yloxymethyl]-3-phenyl-pyridazine;
1-[7-(2,5-dichloro-thiophen-3-ylmethoxy)-naphthalen-1-yl]-4-methyl-piperazine;
3-methyl-5-[8-(4-methyl-piperazin-1-yl)-naphthalen-2-yloxymethyl]-pyridazine;
2-[8-(4-methyl-piperazin-1-yl)-naphthalen-2-yloxymethyl]-benzooxazole;
5-methoxy-2-[8-(1-methyl-piperidin-4-yl)-naphthalen-2-yloxymethyl]-benzooxazole;
2-{1-[8-(4-methyl-piperazin-1-yl)-naphthalen-2-yloxy]-ethyl}-benzooxazole;
2-[8-(4-methyl-piperazin-1-yl)-naphthalen-2-yloxymethyl]-6-trifluoromethyl-benzothiazole;
6-[8-(4-methyl-piperazin-1-yl)-naphthalen-2-yloxymethyl]-3H-benzooxazol-2-one;
7-[8-(4-methyl-piperazin-1-yl)-naphthalen-2-yloxymethyl]-benzo[d]isothiazole;
6-fluoro-7-[8-(4-methyl-piperazin-1-yl)-naphthalen-2-yloxymethyl]-benzo[d]isoxazole;
1-[7-(5-tert-butyl-thiophen-3-ylmethoxy)-naphthalen-1-yl]-4-methyl-piperazine;
1-methyl-4-[7-(4-methyl-5-phenyl-thiophen-3-ylmethoxy)-naphthalen-1-yl]-piperazine;
1-methyl-4-{7-[5-(2'-methyl-biphenyl-4-yl)-thiophen-3-ylmethoxy]-naphthalen-1-yl}-piperazine;
1-methyl-4-[7-(5-p-tolyl-thiophen-2-ylmethoxy)-naphthalen-1-yl]-piperazine;
1-methyl-4-[7-(5-methyl-thiophen-2-ylmethoxy)-naphthalen-1-yl]-piperazine;
1-[7-(3,5-dichloro-thiophen-2-ylmethoxy)-naphthalen-1-yl]-4-methyl-piperazine;
N-{2-[8-(1-methyl-piperidin-4-yl)-naphthalen-2-yloxymethyl]-5-phenyl-thiophen-3-yl}-acetamide;
1-{7-[4-(4-chloro-phenyl)-thiophen-2-ylmethoxy]-naphthalen-1-yl}-4-methyl-piperazine;
1-methyl-4-[7-(5-methyl-thiophen-2-ylmethoxy)-naphthalen-1-yl]-piperidine;
1-methyl-4-[7-(1-methyl-5-phenyl-1H-pyrrol-2-ylmethoxy)-naphthalen-1-yl]-piperazine;
1-methyl-4-[7-(1,4,5-trimethyl-1H-pyrrol-2-ylmethoxy)-naphthalen-1-yl]-piperazine;
1-[7-(5-isopropyl-1-methyl-1H-pyrrol-2-ylmethoxy)-naphthalen-1-yl]-4-methyl-piperazine;
1-methyl-4-[7-(1-methyl-5-phenyl-1H-pyrrol-2-ylmethoxy)-naphthalen-1-yl]-piperidine;
1-{7-[5-(4-chloro-phenyl)-1-methyl-1H-pyrrol-3-ylmethoxy]-naphthalen-1-yl}-4-methyl-piperazine;
1-{7-[4-(2-methoxy-phenyl)-1-methyl-1H-pyrrol-2-ylmethoxy]-naphthalen-1-yl}-4-methyl-piperazine;
1-methyl-4-[7-(3-phenyl-isoxazol-5-ylmethoxy)-naphthalen-1-yl]-piperazine;
4-{7-[3-(2,4-dichloro-phenyl)-isoxazol-5-ylmethoxy]-naphthalen-1-yl}-1-methyl-piperidine;
1-methyl-4-[7-(4-methyl-3-phenyl-isoxazol-5-ylmethoxy)-naphthalen-1-yl]-piperazine;
1-methyl-4-{7-[4-(3-trifluoromethyl-phenyl)-thiophen-2-ylmethoxy]-naphthalen-1-yl}-piperazine;
1-[7-(3-isopropyl-isoxazol-5-ylmethoxy)-naphthalen-1-yl]-4-methyl-piperazine;
1-{7-[3-(3-methoxy-phenyl)-isothiazol-5-ylmethoxy]-naphthalen-1-yl}-4-methyl-piperazine;
1-methyl-4-[7-(3-phenethyl-isothiazol-5-ylmethoxy)-naphthalen-1-yl]-piperazine;
1-methyl-4-[7-(5-phenyl-isothiazol-3-ylmethoxy)-naphthalen-1-yl]-piperazine;
4-{7-[5-(4-chloro-phenyl)-isothiazol-3-ylmethoxy]-naphthalen-1-yl}-1-isopropyl-piperidine;
1-isopropyl-4-{7-[5-(3-trifluoromethyl-phenyl)-isoxazol-3ylmethoxy]-naphthalen-1-yl}-piperazine;
1-methyl-4-{7-[1-(5-phenyl-isoxazol-3-yl)-ethoxy]-naphthalen-1-yl}-piperazine;
1-methyl-4-[7-(3-methyl-2-phenyl-3H-imidazol-4-ylmethoxy)-naphthalen-1-yl]-piperazine;
1-methyl-4-[7-(1-methyl-5-phenyl-1H-imidazol-2-ylmethoxy)-naphthalen-1-yl]-piperazine;
1-ethyl-4-[7-(1-phenyl-1H-imidazol-4-ylmethoxy)-naphthalen-1-yl]-piperazine;
1-methyl-4-[7-(5-methyl-4-phenyl-thiophen-2-ylmethoxy)-naphthalen-1-yl]-piperazine;
1-{7-[2-(4-chloro-phenyl)-oxazol-5-ylmethoxy]-naphthalen-1-yl}-4-methyl-piperazine;

1-methyl-4-[4-methyl-7-(2-phenyl-oxazol-5-ylmethoxy)-naphthalen-1-yl]-piperazine;
4-{7-[2-(3-chloro-phenyl)-oxazol-5-ylmethoxy]-naphthalen-1-yl}-1-methyl-piperidine;
1-[7-(2-tert-butyl-oxazol-5-ylmethoxy)-naphthalen-1-yl]-4-methyl-piperazine;
1-methyl-4-[7-(2-phenyl-thiazol-5-ylmethoxy)-naphthalen-1-yl]-piperazine;
1-isobutyl-4-[7-(4-methyl-2-phenyl-thiazol-5-ylmethoxy)-naphthalen-1-yl]-piperidine;
4-{7-[2-(4-methoxy-phenyl)-thiazol-5-ylmethoxy]-naphthalen-1-yl}-piperazine-1-carboxylic acid ethyl ester;
1-{7-[5-(3,4-dichloro-phenyl)-thiazol-2-ylmethoxy]-naphthalen-1-yl}-4-methyl-piperazine;
1-[7-(5-benzyl-thiazol-2-ylmethoxy)-naphthalen-1-yl]-4-methyl-piperazine;
1-methyl-4-[7-(5-p-tolyl-oxazol-2-ylmethoxy)-naphthalen-1-yl]-piperazine;
1-[7-(4-tert-butyl-thiophen-2-ylmethoxy)-naphthalen-1-yl]-4-methyl-piperazine;
1-methyl-4-[7-(4-methyl-5-phenyl-oxazol-2-ylmethoxy)-naphthalen-1-yl]-piperazine;
1-[7-(5-isopropyl-oxazol-2-ylmethoxy)-naphthalen-1-yl]-4-methyl-piperazine;
4-{7-[5-(2-methoxy-phenyl)-oxazol-2-ylmethoxy]-naphthalen-1-yl}-1-methyl-piperidine;
1-methyl-4-[7-(3-phenyl-[1,2,4]oxadiazol-5-ylmethoxy)-naphthalen-1-yl]-piperazine;
1-[4-chloro-7-(3-phenyl-[1,2,4]oxadiazol-5-ylmethoxy)-naphthalen-1-yl]-4-methyl-piperazine;
1-{7-[3-(4-chloro-phenyl)-[1,2,4]oxadiazol-5-ylmethoxy]-naphthalen-1-yl}-4-cyclopropyl-piperazine;
1-isopropyl-4-{7-[3-(2-methoxy-phenyl)-[1,2,4]oxadiazol-5-ylmethoxy]-naphthalen-1-yl}-piperazine;
1-benzyl-4-{7-[3-(4-trifluoromethyl-phenyl)-[1,2,4]oxadiazol-5-ylmethoxy]-naphthalen-1-yl}-piperazine;
4-[7-(3-phenyl-[1,2,4]oxadiazol-5-ylmethoxy)-naphthalen-1-yl]-piperazine-1-carboxylic acid ethyl ester;
1-methyl-4-{7-[3-(2'-methyl-biphenyl-4-yl)-[1,2,4]oxadiazol-5-ylmethoxy]-naphthalen-1-yl}-piperazine;
1-[7-(5-chloro-3,4-dimethyl-thiophen-2-ylmethoxy)-naphthalen-1-yl]-4-methyl-piperazine;
4-[7-(3-cyclohexyl-[1,2,4]oxadiazol-5-ylmethoxy)-naphthalen-1-yl]-1-methyl-piperidine;
1-methyl-4-{7-[1-(3-phenyl-[1,2,4]oxadiazol-5-yl)-ethoxy]-naphthalen-1-yl}-piperazine;
1-methyl-4-{7-[2-(3-phenyl-[1,2,4]oxadiazol-5-yl)-ethoxy]-naphthalen-1-yl}-piperazine;
1-ethyl-4-{7-[3-(4-fluoro-phenyl)-[1,2,4]oxadiazol-5-ylmethoxy]-naphthalen-1-yl}-4-methyl-piperidine;
1-methyl-4-[7-(3-phenyl-[1,2,4]oxadiazol-5-ylmethoxy)-naphthalen-1-yl]-piperidine;
1-methyl-4-[7-(3-phenyl-[1,2,4]thiadiazol-5-ylmethoxy)-naphthalen-1-yl-piperazine;
1-methyl-4-{7-[1-(3-phenyl-[1,2,4]thiadiazol-5-yl)-ethoxy]-naphthalen-1-yl}-piperazine;
1-methyl-4-{7-[3-(4-trifluoromethoxy-phenyl)-[1,2,4]thiadiazol-5-ylmethoxy]-naphthalen-1-yl}-piperidine;
1-methyl-4-[7-(4-phenyl-thiophen-2-ylmethoxy)-naphthalen-1-yl]-piperidine;
1-{7-[3-(4-methoxy-phenyl)-[1,2,4]thiadiazol-5-ylmethoxy]-2-methylnaphthalen-1-yl)}-4-methyl-piperazine;
1-methyl-4-[7-(5-phenyl-[1,2,4]thiadiazol-3-ylmethoxy)-naphthalen-1-yl]-piperazine;
1-{7-[5-(4-chloro-phenyl)-[1,2,4]thiadiazol-3-ylmethoxy]-naphthalen-1-yl}-4-methyl-piperazine;
1-methyl-4-[7-(5-phenyl-[1,2,4]thiadiazol-3-ylmethoxy)-naphthalen-1-yl]-piperidine;
1-[7-(5-cyclopentyl-[1,2,4]thiadiazol-3-ylmethoxy)-naphthalen-1-yl]-4-methyl-piperazine;
2-{4-[7-(5-phenyl-[1,2,4]thiadiazol-3-ylmethoxy)-naphthalen-1-yl]-piperazin-1-yl}-ethanol;
1-methyl-4-[7-(5-phenyl-[1,2,4]oxadiazol-3-ylmethoxy)-naphthalen-1-yl]-piperazine;
1-{7-[5-(4'-methoxy-biphenyl-4-yl)-[1,2,4]oxadiazol-3-ylmethoxy]-naphthalen-1-yl}-4-methyl-piperazine;
1-[7-(5-isopropyl-[1,2,4]oxadiazol-3-ylmethoxy)-naphthalen-1-yl]-4-methyl-piperazine;
1-ethyl-4-methyl-4-[7-(5-phenyl-[1,2,4]oxadiazol-3-ylmethoxy)-naphthalen-1-yl]-piperidine;
1-methyl-4-[7-(5-phenyl-thiophen-3-ylmethoxy)-naphthalen-1-yl]-piperidine;
1-[7-(5-chloro-benzo[b]thiophen-2-ylmethoxy)-naphthalen-1-yl]-4-methyl-piperazine;
1-methyl-4-[7-(3-methyl-benzo[b]thiophen-2-ylmethoxy)-naphthalen-1-yl]-piperidine;
1-methyl-4-[7-(4,5,6,7-tetrahydro-benzo[b]thiophen-2-ylmethoxy)naphthalen-1-yl]-piperazine;
1-methyl-4-[7-(1-phenyl-1H-[1,2,3]triazol-4-ylmethoxy)-naphthalen-1-yl]-piperidine;
1-methyl-4-[7-(5-methyl-1-phenyl-1H-[1,2,3]triazol-4-ylmethoxy)-naphthalen-1-yl]-piperazine;
4-{7-[1-(4-chloro-phenyl)-1H-[1,2,3]triazol-4-ylmethoxy]-naphthalen-1-yl}-1-methyl-piperidine;
1-methyl-4-[7-(4-methyl-5-phenyl-4H-[1,2,4]triazol-3-ylmethoxy)-naphthalen-1-yl]-piperazine;
4-{7-[5-(4-chloro-phenyl)-thiophen-3-ylmethoxy]-naphthalen-1-yl}-1-methyl-piperidine;
1-[7-(4,5-dimethyl-4H-[1,2,4]triazol-3-ylmethoxy)-naphthalen-1-yl]-4-methyl-piperazine;
1-methyl-4-[7-(4methyl-5-phenyl-4H-[1,2,4]triazol-3-ylmethoxy)-naphthalen-1-yl]-piperidine;
1-[7-(5-benzyl-4-methyl-4H-[1,2,4]triazol-3-ylmethoxy)-naphthalen-1-yl]-4-methyl-piperazine;
1-methyl-4-[7-(2-phenyl-2H-tetrazol-5-ylmethoxy)-naphthalen-1-yl]-piperazine;
4-{7-[2-(4-chloro-phenyl)-2H-tetrazol-5-ylmethoxy]-naphthalen-1-yl}-1-ethyl-piperidine;
1-methyl-4-[7-(6-methyl-4-phenyl-pyridin-2-ylmethoxy)-naphthalen-1-yl]-piperazine;
4-(4-chloro-phenyl)-2-[8-(1-methyl-piperidin-4-yl)-naphthalen-2-yloxymethyl]-pyridine; and
1-[7-(4-tert-butyl-pyridin-2-ylmethoxy)-naphthalen-1-yl]-4-methyl-piperazine.

Other embodiments of the invention include compounds of the formula I wherein p is 1; t is zero; and $R^2$, $R^{23}$ and $R^{24}$ are each hydrogen.

Other embodiments of the invention include compounds of formula I wherein $R^4$ is pyridine, triazole, imidazolo[4,5-b] pyridine, imidazol-2-one[4,5-b]pyridine and benzamidazole.

Other embodiments of the invention include compounds of the formula I wherein $R^4$ is a 5-membered heterocycle selected from 1,2,4-oxadiazolyl, 1,2,4-thiadiazolyl, 1,3,5-oxadiazolyl and 1,3,5-thiadiazolyl.

The present invention also relates to intermediates of the formula

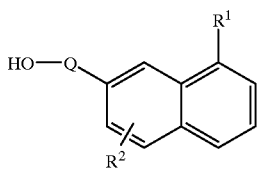

VI' wherein Q is —(CR$^{25}$R$^{26}$), or C=O and R$^1$, R$^2$, R$^{25}$, R$^{26}$ and t are as defined above.

The present invention also relates to a pharmaceutical composition for treating or preventing a condition selected from hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders in a mammal, preferably a human, comprising an amount of a compound of the formula I or a pharmaceutically acceptable salt thereof effective in treating or preventing such condition and a pharmaceutically acceptable carrier.

The present invention also relates to a pharmaceutical composition for treating or preventing disorders serotonergic neurotransmission (e.g., hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders) in a mammal, preferably a human, comprising an amount of a compound of the formula I, or a pharmaceutically acceptable salt thereof, effective in treating or preventing such condition and a pharmaceutically acceptable carrier.

The present invention also relates to a method for treating or preventing a condition selected from hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders in a mammal, preferably a human, comprising administering to a mammal requiring such treatment or prevention an amount of a compound of the formula I, or a pharmaceutically acceptable salt thereof, effective in treating or preventing such condition.

The present invention also relates to a method for treating or preventing disorders the treatment or prevention of which is facilitated by enhanced serotonergic neurotransmission (e.g., hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders) in a mammal, preferably a human, comprising administering to a mammal requiring such treatment or prevention an amount of a compound of the formula I, or a pharmaceutically acceptable salt thereof, effective in treating or preventing such condition.

The present invention also relates to a pharmaceutical composition for treating or preventing a condition selected from hypertension, depression, generalized anxiety disorder, phobias (e.g., agoraphobia, social phobia and simple phobias), posttraumatic stress syndrome, avoidant personality disorder, premature ejaculation, eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders in a mammal, preferably a human, comprising a serotonin receptor antagonizing or agonizing effective amount of a compound of the formula I, or a pharmaceutically acceptable salt thereof, and a pharmaceutically acceptable carrier.

The present invention also relates to a pharmaceutical composition for treating or preventing disorders the treatment or prevention of which is facilitated by enhanced serotonergic neurotransmission (e.g., hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders) in a mammal, preferably a human, comprising a serotonin receptor antagonizing or agonizing effective amount of a compound of the formula I, or a pharmaceutically acceptable salt thereof, and a pharmaceutically acceptable carrier.

The present invention also relates to a method for treating or preventing a condition selected from hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders in a mammal, preferably a human, comprising administering to a mammal requiring such treatment or prevention a serotonin receptor antagonizing or agonizing effective amount of a compound of the formula I or a pharmaceutically acceptable salt thereof.

The present invention also relates to a method for treating or preventing disorders the treatment or prevention of which is facilitated by enhanced serotonergic neurotransmission (e.g., hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders) in a mammal, preferably a human, comprising administering to a mammal requiring such treatment or prevention a serotonin receptor antagonizing or agonizing effective amount of a compound of the formula I or a pharmaceutically acceptable salt thereof.

The present invention relates to a pharmaceutical composition for treating or preventing disorders the treatment or prevention of which is facilitated by enhanced serotonergic neurotransmission in a mammal, preferably a human, comprising:

a) a pharmaceutically acceptable carrier;

b) a compound of the formula I or a pharmaceutically acceptable salt thereof; and c) a 5-HT re-uptake inhibitor, preferably sertraline, or a pharmaceutically acceptable salt thereof;

wherein the amounts of each active compound (i.e., the compund of formula I and the 5-HT re-uptake inhibitor) is such that the combination is effective in treating or preventing such condition.

The present invention also relates to a method for treating or preventing disorders the treatment or prevention of which is facilitated by enhanced serotonergic neurotransmission in a mammal, preferably a human, comprising administering to said mammal requiring such treatment or prevention:

a) a compound of the formula I, defined above, or a pharmaceutically acceptable salt thereof; and b) a 5-HT re-uptake inhibitor, preferably sertraline, or a pharmaceutically acceptable salt thereof;

wherein the amounts of each active compound (i.e., the compound of formula I and the 5-HT re-uptake inhibitor) is such that the combination is effective in treating or preventing such condition.

"Enhanced serotonergic neurotransmission," when used herein, refers to increasing or improving the neuronal process whereby serotonin is released by a pre-synaptic cell upon excitation and crosses the synapse to stimulate or inhibit the post-synaptic cell.

"Chemical dependency," as used herein, means an abnormal craving or desire for, or an addiction to a drug. Such drugs are generally administered to the affected individual by any of a variety of means of administration, including oral, parenteral, nasal or by inhalation. Examples of chemical dependencies treatable by the methods of the present invention are dependencies on alcohol, nicotine, cocaine, heroin, phenolbarbitol, and benzodiazepines (e.g., Vallium (trademark)). "Treating a chemical dependency," as used herein, means reducing or alleviating such dependency.

Sertraline, (1S-cis)-4-(3,4-dichlorophenyl)-1,2,3,4-tetrahydro-N-methyl-1-naphthalenamine, as used herein has the chemical formula $C_{17}H_{17}NCl_2$ and the following structural formula

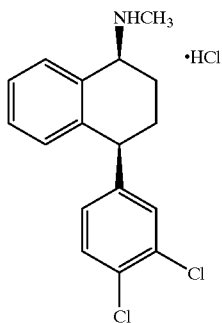

Its synthesis is described in U.S. Pat. No. 4,536,518, assigned to Pfizer Inc. Sertraline hydrochloride is useful as an antidepressant and anorectic agent, and is also useful in the treatment of depression, chemical dependencies, anxiety obsessive compulsive disorders, phobias, panic disorder, post traumatic stress disorder, and premature ejaculation,

DETAILED DESCRIPTION OF THE INVENTION

Compounds of the formula I may be prepared according to the following reaction Schemes and discussion. Unless otherwise indicated, a, e, m, n, p, t, $R^1$, $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$, $R^{25}$, $R^{26}$, $R^{27}$, A, B, D, E, F, G, I, J, K, L, Z, M and O and the structural formulae I, II, III, IV, V, VI', XV, XVI and XVII in the reaction Schemes and discussions that follow are as defined above.

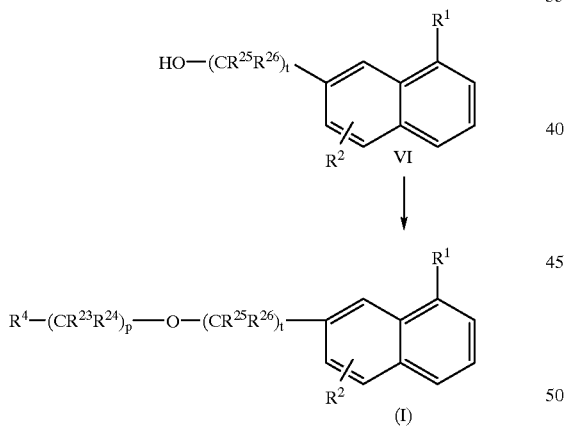

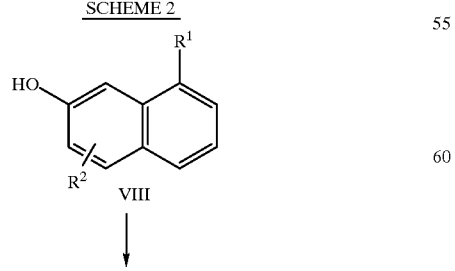

-continued

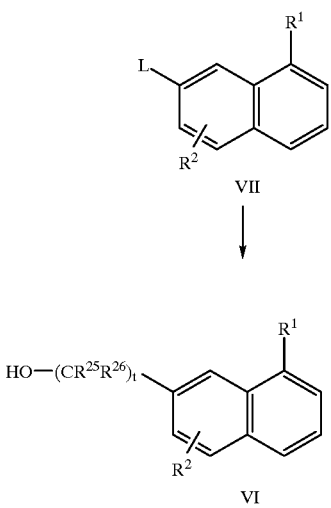

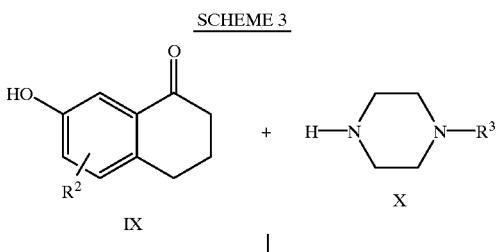

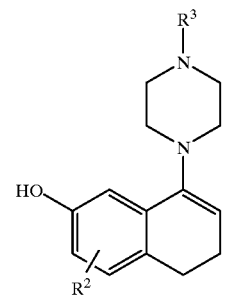

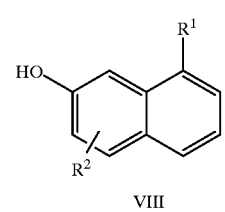

SCHEME 4

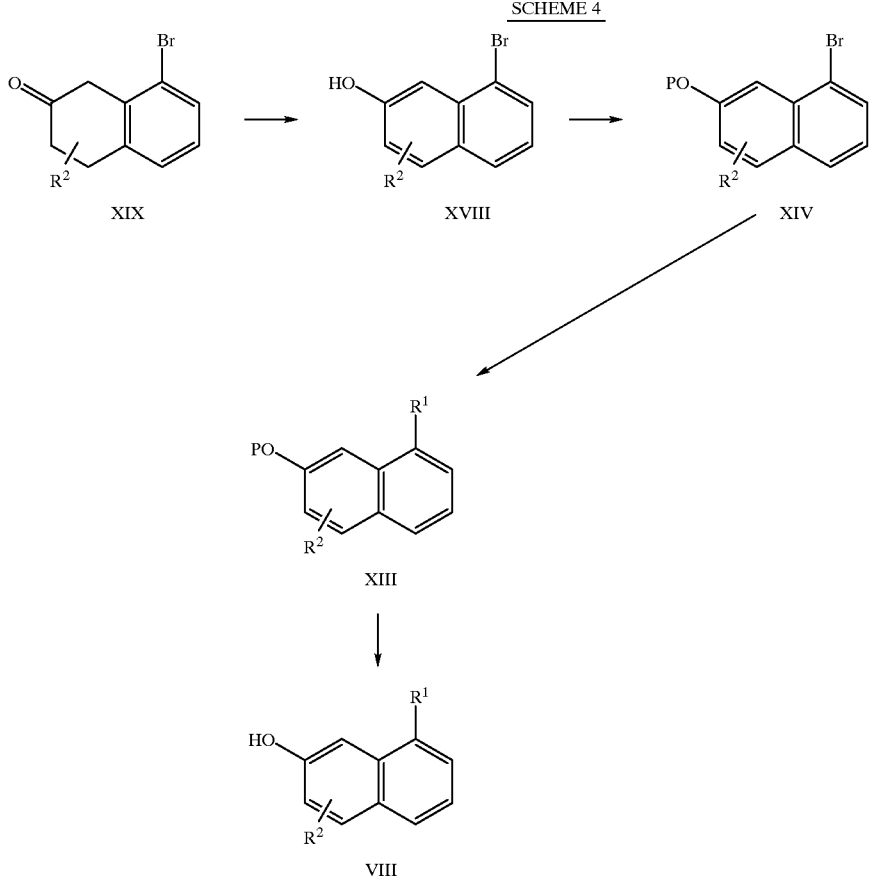

SCHEME 5

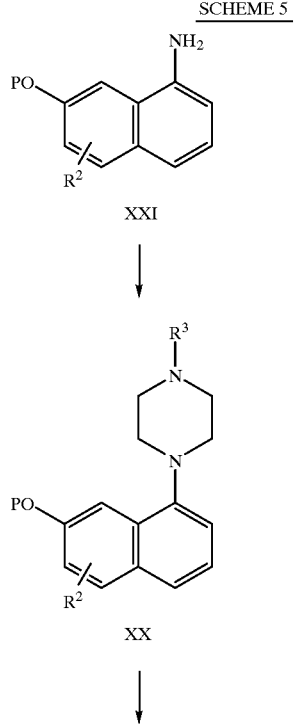

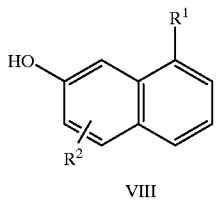

-continued

VIII

According to Scheme 1, compounds of the general formula I may be prepared by alkylation of an intermediate of formula VI with a compound of the general formula $$R^4-(CR^{23}R^{24})_p-Y$$

wherein Y is a leaving group such as chloro, bromo, iodo, $-OSO_2Ph$, $-OSO_2PhCH_3$, $-OSO_2CH_3$, $-OSO_2CF_3$ (trifluoromethanesulfonyloxy) or OH.

The alkylation reaction may be carried out in the presence of a base such as triethylamine, sodium or potassium carbonate or bicarbonate, sodium or potassium hydride or 4-dimethylaminopyridine. A suitable solvent for the reaction can be selected from non-protic solvents such as diethyl ether, tetrahydrofuran (THF), 1,4-dioxane, chloroform ($CHCl_3$), dichloromethane ($CH_2Cl_2$), N,N-dimethylformamide (DMF), N,N-dimethylacetamide, N-methypyrrolidinone, benzene, toluene or xylenes. The reaction can be performed at a temperature of about 0° C. to about the boiling point of the solvent employed (e.g. about 100° C. for DMF) and at a pressure of about one to about three atmospheres.

Preferably, the reaction is conducted in N,N-dimethylformamide with sodium hydride as a base at a temperature of about 25–100° C. and one atmosphere of pressure.

Alternatively, compounds of the formula I can be prepared from compounds of formula VI by Mitsunobu chemistry. According to this method, compounds of formula VI are reacted with alcohols, for example, 2-pyrazinemethanol or 4-pyrazolemethanol in the presence of triphenylphosphine and a dialkyl azodicarboxylate, preferably diethyl azodicarboxylate. Mitsunobu reactions are known in the art, for example, as disclosed in *Synthesis*, 1981, 1.

According to the methods of Scheme 2, compounds of the formula VI can be prepared from compounds of the formula VIII. Compounds of the formula VI can then be transformed into compounds of the formula I according to the procedures of Scheme 1.

Compounds of the formula VIII are converted into a triflate ($CF_3SO_3$) of the formula VII wherein L is $CF_3SO_3^-$ by reaction with an activated form of triflic acid, for example, triflic anhydride, acid chloride or N-phenyltrifluoromethanesulfonimide, preferably triflic anhydride. Typically, this reaction is performed in the presence of a base, such as, for example, triethylamine or diisopropylethylamine, preferably triethylamine. The reaction may be run in an inert solvent, such as tetrahydrofuran or methylene chloride, at a temperature of from about −78° C. to about 25° C., preferably below about 0° C. This procedure is known in the art, as shown, for example, in *J. Amer. Chem. Soc.*, 1987, 109, 5478.

The compound of formula VII can then be transformed into a compound of formula VI] wherein L is an ester of the formula —$CO_2R$, wherein R is ($C_1$–$C_6$) alkyl or benzyl, by reaction with carbon monoxide in the presence of a palladium catalyst in an alcohol solvent such as methanol. The catalyst may be selected from those typically employed for the so-called Heck reaction (palladium acetate, palladium chloride, bis (acetonitrile) palladium chloride, for example). The reaction is carried out neat or in an alcohol solvent such as methanol, ethanol, isopropanol, butanol or benzyl alcohol. The reaction is conveniently run at 20° C. to 100° C., preferably 60° C. to 100° C. The details of reactions of this type have been well described in the literature (*Organic Reactions* 1982, 27, 345).

The ester of formula VII wherein L is —$CO_2R$ can then be reduced with a catalyst to form a hydroxymethyl compound of formula VI wherein t is one and $R^{25}$ and $R^{26}$ are hydrogen. The reduction of an ester group to a hydroxymethyl group is well known to those of ordinary skill in the art. Preferably, the ester is reduced using borane tetrahydrofuran complex in an inert solvent such as tetrahydrofuran (THF).

This alcohol of formula VI wherein t is one can be converted into other alcohols of formula VI by processes well known to those of ordinary skill in the art. Specifically, the alcohol of formula VI wherein t is one can be converted into a compound of formula VI wherein t is two by reacting the alcohol with an activating group such as methanesulfonyl chloride in triethylamine (TEA) in an inert solvent such as methylene chloride ($CH_2Cl_2$) to generate an activated leaving group in which the alcohol has been replaced by $CH_3SO_3^-$, and then treating the activated leaving group with a nucleophile such as sodium or potassium cyanide in a solvent such as dimethyl sulfoxide to form a cyano intermediate of the formula

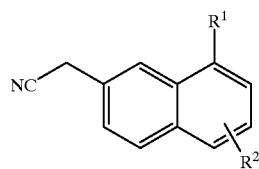

The cyano group can then be hydrolyzed under acidic conditions to produce a carboxylic acid. The acid can in turn be converted into an ester by methods familiar to those of ordinary skill in the art. For example, the acid can be reacted with an alcohol of the formula ROH, wherein R is as defined above, in the presence of an acid catalyst to produce an ester. The ester can be reduced to the compound of formula VI wherein t is two in a manner similar to the reduction of the ester to the compound of formula VI wherein t is one.

According to the methods of Scheme 3, compounds of formula VIII wherein $R^1$ is piperazine are prepared by reaction of an α-tetralone of formula IX with a suitable piperazine of formula X to form an enamine of formula XI, which is then oxidized to the compound of formula VIII.

The enamines of formula XI are generally prepared by reaction of a compound of formula IX with a compound of formula X in the presence of an acid catalyst such as, for example, p-toluenesulfonic acid or titanium tetrachloride. If desired, the water formed as a by-product of the reaction may be effectively removed from the reaction as it is formed by the use of a drying reagent such as molecular sieves or calcium sulfate, or by azeotropic removal employing a Dean Stark trap with a refluxing solvent. The reaction is typically run in a reaction inert solvent such as benzene, toluene, tetrahydrofuran, or methylene chloride, at a temperature of from about −78° C. to about 150° C. When titanium tetrachloride is used as the acid catalyst, the preferred temperature for the reaction is from about −78° C. to about 25° C. When azeotropic water separation is employed, the preferred reaction temperature is the boiling temperature of the particular reaction solvent.

In general, the α-tetralones of formula IX are known in the literature or can be readily prepared by those skilled in the art. A typical preparation is that described for 7-hydroxy-α-tetralone, (*Tetrahedron Lett.*, 1981, 22, 603). Other α-tetralones of formula IX are readily prepared using the alkylation, acylation, and organometallic reactions described herein and in standard synthesis texts, for example *Organic Synthesis*, Wiley, New York. The piperazines of formula X are commercially available or can be made using methods known in the art.

The enamines of formula XI may be converted to compounds of formula VIII by an oxidative process. The reaction may be carried out using a variety of methods known in the art. Among the acceptable oxidizing agents are noble metal catalysts such as palladium or platinum on activated carbon if desired, chloranil, and sulfur. Preferably, the oxidizing agent is palladium on activated carbon. The reactions can be carried out in a reaction inert solvent for example, toluene, xylene, tetrahydrofuran, methylene chloride, preferably toluene or xylene, however a solvent is not always necessary, especially for oxidations carried out with elemental sulfur. The preferable solvent is toluene. The oxidation reactions generally proceed at a temperature of about 0° C. to about 250° C. Preferred temperatures for the oxidation depend on the particular oxidant in use and are about 60° C. to about 150° C. for noble metal catalytic oxidation, about 150° C. to about 250° C. for sulfur oxidation and about 0° C. to about 100° C. for chloranil oxidations.

The compounds of formula VIII wherein $R^1$ is a group of the formula III, IV or V (i.e., tetrahydropyridine, piperidine, or azacycloalkylmethyl) can be made from 8-bromo-β-tetralone according to the procedures in U.S. Pat. No. 4,897,405, or by the methods described in Scheme 4.

According to Scheme 4, an 8-bromo-β-tetralone of the formula XIX is first oxidized (dehydrogenated) to form a 7-hydroxy-1-bromo-naphthalene of the formula XVIII using an oxidizing reagent, such as, for example, elemental sulfur as described above for the oxidation of the enamine of formula XI in Scheme 3. An appropriate protecting group is then used to protect the hydroxyl group to form a compound of the formula XIV. Formation and selection of the appropriate protecting group are within the knowledge of one skilled in the art (e.g., Greene and Wuts, *Protective Groups in Organic Synthesis*, 2nd Edition, Wiley, New York, 1991). Preferably, the hydroxy protecting group is the t-butyl dimethylsilyl group.

After the hydroxy group has been protected, the bromo naphthalenes of the formula XIV are treated with a vinyl-stannane of the formula

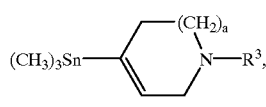

IIIb

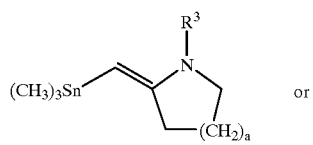

IVb

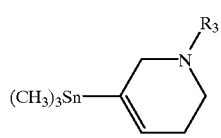

Vb in the presence of a catalyst, preferably tetrakis(triphenylphosphine)palladium ($(Ph_3P)_4Pd$) or tris(dibenzylidene acetone)dipalladium ($Pd_2(dba)_3$), a ligand-less catalyst (*Tet. Letters*, 34, 4243 (1991)), either alone or with an added phosphine or arsine ligand (*JACS*, 113, 9585 (1991)) in a Stille reaction to form a compound of the formula XIII wherein $R^1$ is IIIb, IVb or Vb IIIb

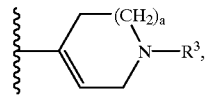

IVa

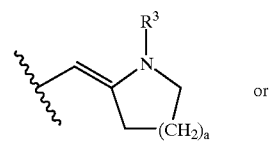

Vb

The procedures and conditions to carry out this reaction are known to those in the art, for example, in *Angew. Chem. Int. Ed. Engl.*, 25, 508 (1986). A variation of this reaction in which a triflate is used is also known in the art, for example, in *J. Amer. Chem. Soc.*, 109, 5478 (1987). A further variation of this type of process which uses an alkyl or aryl halide in the presence of carbon monoxide gas and a palladium catalyst is also known, for example, in *J. Amer. Chem. Soc.*, 110, 1557 (1988).

The hydroxy protecting group in formula XIII can then be removed to form a compound of the formula VIII. Selection of the appropriate reagents and conditions to remove the protecting group is within the knowledge of one skilled in the art (e.g., Greene and Wuts, *Protective Groups in Organic Synthesis*, 2nd Edition, Wiley, New York, 1991).

Compounds of formula I wherein $R^1$ is a saturated heterocycle (i.e., piperidine) can be prepared by catalytic hydrogenation of a compound of formula XIII, using standard methods known in the art, generally with palladium on carbon as the catalyst. Compounds of formula I wherein $R^1$ is an enantiomerically pure group of the formula IIIa, IVa or Va as described above in the summary of the invention can be prepared by stereoselective reduction of a compound of the formula XIII. The stereoselective reduction is effected by treatment of the compound of the formula XIII with a binaphthyl-ruthenium catalyst such as [(R)-2,2$^1$-bis(diphenylphosphino)-1-, 1$^1$-binaphthyl]ruthenium diacetate according to the method of Takaya et. al. in *Organic Synthesis*, 72 D. L. Coffen editor, 74–85, (1993).

Alternatively, the 1-bromo-7-hydroxy-protected-naphthalene compounds of formula XIV from Scheme 4 may be treated with alkyllithium reagents, such as for example, butyllithium, sec-butyllithium or tert-butyllithium, preferably butyllithium in an inert solvent, as shown below,

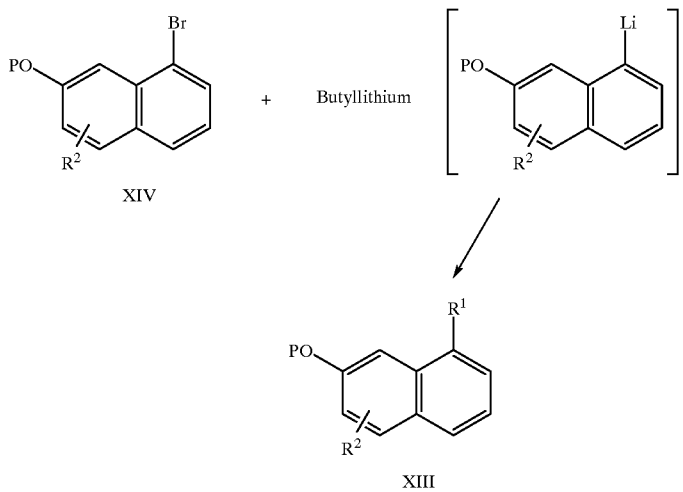

Suitable solvents include, for example, ether or tetrahydrofuran, preferably tetrahydrofuran. Reaction temperatures range from about −110° C. to about 0° C. The intermediate lithium anions thus formed may then be further reacted with a suitable electrophile, selection of which depends on the substituents at the $R^1$ and $R^2$ positions. Suitable electrophiles to prepare hydroxy protected compounds of formula XIII include, for example, carbonyl derivatives or alkylating agents such as 1-BOC4-piperidone, 1-BOC-prolinal or 1-FMOC-2-chloromethylpyrrolidine. BOC is understood by those of ordinary skill in the art to refer to butoxycarbonyl. FMOC is understood by those of skill in the art to refer to trifluoromethoxycarbonyl.

After the bromo substituent has been functionalized, the hydroxyl protecting group may be removed using procedures well know to those skilled in the art to form compounds of the formula VIII wherein $R^1$ is tetrahydropyridine, piperidine, or azacycloalkylmethyl.

The free hydroxyl group may then be derivatized to form compounds of the formula VI as described in Scheme 2.

Compounds of the formula VIII can also be prepared according to the methods of Scheme 5 by condensation of a protected or unprotected hydroxy compound of the formula XXI with a compound of the formula

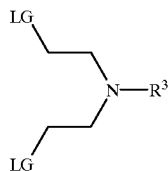

LG is an $S_n 2$ leaving group such as chloro, bromo, iodo, −$OSO_2Ph$, —$OSO_2PhCH_3$, —$OSO_2CH_3$, —$OSO_2CF_3$ to form a hydroxy protected compound of the formula XX. The reaction is performed in an inert solvent in the presence of base. The preferred leaving group is iodo, and is prepared in situ from the chloro derivative using stoichiometric amounts of sodium or potassium iodide in the reaction mixture. Suitable solvents include ($C_1$ to $C_4$) alcohols, dimethyl sulfoxide, N,N-dimethylformamide, N-methylpyrrolidinone, acetonitrile, and acetone. Acetonitrile is the preferred solvent. Suitable bases include sodium hydroxide, potassium hydroxide, triethylamine, sodium or potassium carbonate, cesium carbonate, and sodium or potassium hydrogen carbonate. Sodium hydrogen carbonate is the preferred base. The reaction is usually conducted at a temperature of about 50° C. to about 154° C., preferably at about 70–90° C.

The hydroxy protected compound of the formula XX can be deprotected according to methods well known to those of ordinary skill in the art, to form a compound of the formula VIII (e.g., Greene and Wuts, *Protective Groups in Organic Synthesis,* 2nd Edition, Wiley, New York 1991). Compounds of the formula VIII can be converted into compounds of the formula I according to the methods of Schemes 1 and 2.

Compounds of the formula I wherein $R^2$ is other than hydrogen can be prepared from other compounds of formula I wherein $R^2$ is bromine by methods well known to those of ordinary skill in the art. Compounds of formula I wherein $R^2$ is bromine can be made by processes analogous to those described in Preparation 11.

Unless indicated otherwise, the pressure of each of the above reactions is not critical. Generally, the reactions will be conducted at a pressure of about one to about three atmospheres, preferably at ambient pressure (about one atmosphere).

The compounds of the formula I which are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent, and subsequently convert the free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent such as methanol or ethanol. Upon careful evaporation of the solvent, the desired solid salt is obtained.

The acids which are used to prepare the pharmaceutically acceptable acid addition salts of the base compounds of this invention are those which form non-toxic acid addition salts. i.e., salts containing pharmacologically acceptable anions, such as hydrochloride, hydrobromide, hydroiodide, nitrate, sulfate or bisulfate, phosphate or acid phosphate, acetate, lactate, citrate or acid citrate, tartrate or bitartrate, succinate, maleate, fumarate, gluconate, saccharate, benzoate. methanesulfonate and pamoate [i.e., 1,1'-methylene-bis-(2-hydroxy-3-naphthoate)] salts.

Those compounds of the formula I which are also acidic in nature, e.g., where $R_2$ contains a carboxylate, are capable of forming base salts with various pharmacologically acceptable cations. Examples of such salts include the alkali metal or alkaline-earth metal salts and particular, the sodium and potassium salts. These salts are all prepared by conventional techniques. The chemical bases which are used as reagents to prepare the pharmaceutically acceptable base salts of this invention are those which form non-toxic base salts with the herein described acidic compounds of formula I. These non-toxic base salts include those derived from such pharmacologically acceptable cations as sodium, potassium, calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product yields.

The compounds of the formula I and the pharmaceutically acceptable salts thereof (hereinafter, also referred to as "the active compounds") are useful psychotherapeutics and are potent serotonin ($5\text{-}HT_1$) agonists and antagonists and may be used in the treatment of hypertension, depression, generalized anxiety disorder, phobias (e.g., agoraphobia, social phobia and simple phobias), posttraumatic stress syndrome, avoidant personality disorder, sexual dysfunction (e.g., premature ejaculation), eating disorders (e.g., anorexia nervosa and bulimia nervosa), obesity, chemical dependencies (e.g., addictions to alcohol, cocaine, heroin, phenolbarbitol, nicotine and benzodiazepines), cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders. These compounds are also useful as vasodilators.

The affinities of the compounds of this invention for the various serotonin-1 receptors are evaluated using standard radioligand binding assays as described in the literature, The $5\text{-}HT_{1A}$ affinity can be measured using the procedure of Hoyer et al. (*Brain Res.*, 1986, 376, 85). The $5\text{-}HT_{1C}$ affinity can be measured using the procedure of Pazos et al. (*Eur. J. Pharmacol.*, 1985, 106, 539). The $5\text{-}HT_{1D}$ affinity can be measured using the procedure of Heuring and Peroutka (*J. Neurosci.*, 1987, 7, 894).

The in vitro activity of the compounds of the present invention at the $5\text{-}HT_{1D}$ binding site may be determined according to the following procedure. Bovine caudate tissue may be homogenized and suspended in 20 volumes of a buffer containing 50 mM TRIS.hydrochloride (tris [hydroxymethyl]aminomethane hydrochloride) at a pH of 7.7. The homogenate may then be centrifuged at 45,000G for 10 minutes. The supernatent can then be discarded and the resulting pellet resuspended in approximately 20 volumes of 50 mM TRIS.hydrochloride (HCl) buffer at pH 7.7. This suspension may then be pre-incubated for 15 minutes at 37° C. after which time the suspension may be centrifuged again at 45,000G for 10 minutes and the supernatent should be discarded. The resulting pellet (approximately 1 g), may be resuspended in 150 ml of a buffer of 15 mM TRIS.hydrochloride (HCl) containing 0.01 percent ascorbic acid with a final pH of 7.7 and also containing 10 $\mu$M pargyline and 4 mM calcium chloride ($CaCl_2$). The suspension should be kept on ice at least 30 minutes prior to use.

The inhibitor, control or vehicle can then be incubated according to the following procedure. To 50 $\mu$l of a 20 percent dimethylsulfoxide (DMSO)/80 percent distilled water solution may be added 200 $\mu$l of tritiated 5-hydroxytryptamine (2 nM) in a buffer of 50 mM TRIS.hydrochloride containing 0.01 percent ascorbic acid at pH 7.7 and containing 10 $\mu$M pargyline and 4 $\mu$M calcium chloride, plus 100 nM of 8-hydroxy-DPAT (dipropylaminotetraline) and 100 nM of mesulergine. To this mixture may then be added 750 $\mu$l of bovine caudate tissue and the resulting suspension may be vortexed to ensure a homogenous suspension. The suspension can then be incubated in a shaking water bath for 30 minutes at 25° C. After incubation is complete, the suspension can be filtered using glass fiber filters (e.g., Whatman GF/B-filters™). The pellet can then be washed three times with 4 ml of a buffer of 50 mM TRIS.hydrochloride at pH 7.7. The pellet can then be placed in a scintillation vial with 5 ml of of scintillation fluid (aquasol 2,™) and allowed to sit overnight. A percent inhibition can be calculated for each dose of the compound. An $IC_{50}$ value can then be calculated from the percent inhibition values.

The activity of the compounds of the present invention for $5\text{-}HT_{1A}$ binding ability can be determined according to the following procedure. Rat brain cortex tissue can be homogenized and divided into samples of 1 g lots and diluted with 10 volumes of 0.32 M sucrose solution. The suspension may then be centrifuged at 900G for 10 minutes and the supernate separated and recentrifuged at 70,000G for 15 minutes. The supernate can be discarded and the pellet re-suspended in 10 volumes of 15 mM TRIS.hydrochloride at pH 7.5. The suspension should be allowed to incubate for 15 minutes at 37° C. After pre-incubation is complete the suspension should be centrifuged at 70,000G for 15 minutes and the supernate discarded. The resulting tissue pellet may be resuspended in a buffer of 50 mM TRIS.hydrochloride at pH 7.7 containing 4 mM of calcium chloride and 0.01 percent ascorbic acid. The tissue should be stored at −70° C. until ready for an experiment. The tissue can be thawed immediately prior to use, diluted with 10 $\mu$m pargyline and kept on ice.

The tissue may then be incubated according to the following procedure. Fifty microliters of control, inhibitor, or vehicle (1 percent DMSO final concentration), may be prepared at various dosages. To this solution may be added 200 $\mu$l of tritiated DPAT at a concentration of 1.5 nM in a buffer containing 50 mM TRIS.hydrochloride at pH 7.7 containing 4 mM calcium chloride, 0.01 percent ascorbic acid and pargyline. To this solution may then be added 750 $\mu$l of tissue and the resulting suspension vortexed to ensure homogeneity. The suspension may then be incubated in a shaking water bath for 30 minutes at 37° C. The solution can then be filtered, washed twice with 4 ml of mM TRIS.hydrochloride at pH 7.5 containing 154 mM of sodium chloride. The percent inhibition may be calculated for each dose of the compound, control or vehicle. An IC$_{50}$ value is calculated from the percent inhibition values.

The compounds of formula I of the present invention described in the following Examples were assayed for 5-HT$_{1A}$ and 5-HT$_{1D}$ affinity using the aforementioned procedures. All of the compounds that were tested had IC$_{50}$s of less than 0.60 μM.

The compounds of the invention can be tested for in vivo activity for antagonism of 5-HT$_{1D}$ agonist-induced hypothermia in Guinea Pigs according to the following procedure.

Male Hartley Guinea pigs from Charles River, weighing 250–275 grams on arrival and 300–600 g. at testing, serve as subjects in the experiment. The Guinea pigs are housed under standard laboratory conditions on a 7 a.m. to 7 p.m. lighting schedule for at least seven days prior to experimentation. Food and water are available ad libitum until the time of testing.

The compounds of the invention can be administered as solutions in a volume of 1 ml/kg. The vehicle used is varied depending on compound solubility. Test compounds are typically administered either sixty minutes orally (p.o.) or 0 minutes subcutaneous (s.c.) prior to the 5-HT$_{1D}$ agonist, which is administered at a dose of 5.6 mg/kg, s.c. Before a first temperature reading is taken, each Guinea pig is placed in a clear plastic shoe box containing wood chips and a metal grid floor and allowed to acclimate to the surroundings for 30 minutes. Animals are then returned to the same shoe box after each temperature reading. Prior to each temperature measurement each animal is firmly held with one hand for a 30-second period. A digital thermometer with a small animal probe is used for temperature measurements. The probe is made of semi-flexible nylon with an epoxy tip. The temperature probe is inserted 6 cm. into the rectum and held there for 30 seconds or until a stable recording is obtained. Temperatures are then recorded.

In p.o. screening experiments, a "pre-drug" baseline temperature reading is made at −90 minutes, the test compound is given at −60 minutes and an additional 30-minute reading is taken. The 5-HT$_{1D}$ agonist is then administered at 0 minutes and temperatures are taken 30, 60, 120 and 240 minutes later.

In subcutaneous screening experiments, a pre-drug baseline temperature reading is made at −30 minutes. The test compound and 5-HT$_{1D}$ agonists are given concurrently and temperatures are taken at 30, 60, 120 and 240 minutes later.

Data are analyzed with two-way analysis of variants with repeated measures in Newman-Keuls post hoc analysis.

U.S. Pat. No. 4,536,518 describes the synthesis, pharmaceutical composition and use of sertraline for depression and is hereby incorporated by reference in its entirety. Sertraline hydrochloride has the chemical formula $C_{17}H_{17}NCl_2$ and the following structural formula

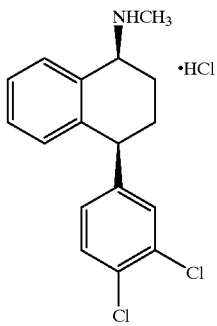

Its synthesis is described in U.S. Pat. No. 4,536,518, assigned to Pfizer Inc. Sertraline hydrochloride is useful as an antidepressant or an anorectic agent, and is also useful in the treatment of depression, chemical dependencies, anxiety-related disorders and premature ejaculation. U.S. Pat. No. 4,536,518 is hereby incorporated by reference in its entirety.

The compounds of formula I may advantageously be used in conjunction with one or more other therapeutic agents, for instance, different antidepressant agents such as tricyclic antidepressants (e.g., amitripyline, dothiepin, doxepin, trimipramine, butripyline, clomipramine, despramine, imipramine, iprindole, lofepramine, nortriptyline or protriptyline), monoamine oxidase inhibitors (e.g., isocarboxazid, phenelzine or tranylcyclopramine) or 5-HT re-uptake inhibitors (e.g., fluvoxamine, sertraline, fluoxetine or paroxetine), and/or with antiparkinsonian agents such as dopaminergic antiparkinsonian agents (e.g., levodopa, preferably in combination with a peripheral decarboxylase inhibitor (e.g., benserazide or carbidopa, or with a dopamine agonist e.g., bromocriptine, lysuride or pergolide). It is to be understood that the present invention covers the use of a compound of general formula (I) or a physiologically acceptable salt or solvate thereof in combination with one or more other therapeutic agents.

5-HT re-uptake inhibitors, preferably sertraline, exihbit positive activity against depression; chemical dependencies; anxiety disorders including panic disorder, generalized anxiety disorder, agoraphobia, simple phobias, social phobia, and post-traumatic stress disorder; obsessive-compulsive disorder; avoidant personality disorder and premature ejaculation in mammals, including humans, due in part to their ability to block the synaptosomal uptake of serotonin.

Preferably, the compounds of the formula I and the pharmaceutically acceptable salts thereof in combination with a 5-HT re-uptake inhibitor (e.g., fluvoxamine, sertraline, fluoxetine or paroxetine), preferably sertraline, or a pharmaceutically acceptable salt or polymorph thereof (herein, the combination of a compound of formula I with a 5-HT re-uptake inhibitor is collectively referred to as "the active combination") are useful psychotherapeutics and may be used in the treatment or prevention of disorders the treatment or prevention of which is facilitated by enhanced serotonergic neurotransmission (e.g., hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive compulsive disorder, panic disorder, memory disorders (e.g., dementia, amnestic disorders, and age-associated memory impairment), Parkinson's diseases (e.g., dementia in Parkinson's disease, neuroleptic-induced Parkinsonism and tardive dyskinesias), endocrine disorders (e.g., hyperprolactinaemia), vasospasm (particularly in the cerebral vasculature), gastrointestinal tract disorders (where changes in motility and secretion are involved) and chronic paroxysmal hemicrania and headache associated with vascular disorders.

The active compounds of the invention can be evaluated as anti-migraine agents by testing the extent to which they mimic sumatriptan in contracting the dog isolated saphenous vein strip [P. P. A. Humphrey et al., *Br. J. Pharmacol.*, 94, 1128 (1988)]. This effect can be blocked by methiothepin, a known serotonin antagonist. Sumatriptan is known to be useful in the treatment of migraine and produces a selective increase in carotid vascular resistance in the anesthetized dog. The pharmacological basis of sumatriptan efficacy has been discussed in W. Fenwick et al., *Br. J. Pharmacol.*, 96, 83

The serotonin 5-$HT_1$ agonist activity can be determined by the in vitro receptor binding assays as described for the 5-$HT_{1A}$ receptor using rat cortex as the receptor source and [$^3$H]-8-OH-DPAT as the radioligand [D. Hoyer et al. *Eur. J. Pharm.*, 118, 13 (1985)] and as described for the 5-$HT_{1D}$ receptor using bovine caudate as the receptor source and [$^3$H]serotonin as the radioligand [R. E. Heuring and S. J. Peroutka, *J. Neuroscience*, 7, 894 (1987)]. Of the active compounds tested, all exhibited an $IC_{50}$ in either assay of 250 nM or less.

Activity of the active combination as antidepressants and related pharmacological properties can be determined by methods (1)–(4) below, which are described in Koe, B. et al., *Journal of Pharmacology and Experimental Therapeutics*, 226 (3), 686–700 (1983). Specifically, activity can be determined by studying (1) their ability to affect the efforts of mice to escape from a swim-tank (Porsolt mouse "behavior despair" test), (2) their ability to potentiate 5-hydroxytryptophan-induced behavioral symptoms in mice in vivo, (3) their ability to antagonize the serotonin-depleting activity of p-chloroamphetamine hydrochloride in rat brain in vivo, and (4) their ability to block the uptake of serotonin, norepinephrine and dopamine by synaptosomal rat brain cells in vitro. The ability of the active combination to counteract reserpine hypothermia in mice in vivo can be determined according to the methods described in U.S. Pat. No. 4,029,731.

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous) or rectal administration or in a form suitable for administration by inhalation or insufflation.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbid acid).

For buccal administration, the composition may take the form of tablets or lozenges formulated in conventional manner.

The active compounds of the invention may be formulated for parenteral administration by injection, including using conventional catheterization techniques or infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in powder form for reconstitution with a suitable vehicle, e.g., sterile pyrogen-free water, before use.

The active compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

A proposed dose of the active compounds of the invention for oral, parenteral or buccal administration to the average adult human for the treatment of the conditions referred to above (e.g., migraine) is 0.1 to 200 mg of the active ingredient per unit dose which could be administered, for example, 1 to 4 times per day.

Aerosol formulations for treatment of the conditions referred to above (e.g., migraine) in the average adult human are preferably arranged so that each metered dose or "puff" of aerosol contains 20 µg to 1000 µg of the compound of the invention. The overall daily dose with an aerosol will be within the range 100 µg to 10 mg. Administration may be several times daily, for example 2, 3, 4 or 8 times, giving for example, 1, 2 or 3 doses each time.

In connection with the use of an active compound of this invention with a 5-HT re-uptake inhibitor, preferably sertraline, for the treatment of subjects possessing any of the above conditions, it is to be noted that these compounds may be administered either alone or in combination with pharmaceutically acceptable carriers by either of the routes previously indicated, and that such administration can be carried out in both single and multiple dosages. More particularly, the active combination can be administered in a wide variety of different dosage forms, i.e., they may be combined with various pharmaceutically-acceptable inert carriers in the form of tablets, capsules, lozenges, troches, hand candies, powders, sprays, aqueous suspension, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for such purposes. In general, the compounds of formula I are present in such dosage forms at concentration levels ranging from about 0.5% to about 90% by weight of the total composition, i.e., in amounts which are sufficient to provide the desired unit dosage and a 5-HT re-uptake inhibitor, preferably sertraline, is present in such dosage forms at concentration levels ranging from about 0.5% to about 90% by weight of the total composition, i.e., in amounts which are sufficient to provide the desired unit dosage. The compounds of this invention may exist in different polymorphic forms, i.e., different crystalline forms.

A proposed daily dose of an active compound of this invention in the combination formulation (a formulation containing an active compound of this invention and a 5-HT re-uptake inhibitor) for oral, parenteral, rectal or buccal administration to the average adult human for the treatment of the conditions referred to above is from about 0.01 mg. to about 2000 mg., preferably from about 0.1 mg. to about 200 mg of the active ingredient of formula I per unit dose which could be administered, for example, 1 to 4 times per day.

A proposed daily dose of a 5-HT re-uptake inhibitor, preferably sertraline, in the combination formulation for oral, parenteral or buccal administration to the average adult human for the treatment of the conditions referred to above is from about 0.1 mg. to about 2000 mg., preferably from about 1 mg. to about 200 mg. of the 5-HT re-uptake inhibitor per unit dose which could be administered, for example, 1 to 4 times per day.

A preferred dose ratio of sertraline to an active compound of this invention in the combination formulation for oral, parenteral or buccal administration to the average adult human for the treatment of the conditions referred to above is from about 0.00005 to about 20,000, preferably from about 0.25 to about 2,000.

Aerosol combination formulations for treatment of the conditions referred to above in the average adult human are preferably arranged so that each metered dose or "puff" of aerosol contains from about 0.01 $\mu$g to about 1000 $\mu$g of the active compound of this invention, preferably from about 1 $\mu$g. to about 10 mg. of such compound. Administration may be several times daily, for example 2, 3, 4 or 8 times, giving for example, 1, 2 or 3 doses each time.

Aerosol formulations for treatment of the conditions referred to above in the average adult human are preferably arranged so that each metered dose or "puff" of aerosol contains from about 0.01 mg. to about 2000 mg. of a 5-HT re-uptake inhibitor, preferably sertraline, preferably from about 1 mg. to about 200 mg of sertraline. Administration may be several times daily, for example 2, 3, 4 or 8 times, giving for example, 1, 2 or 3 doses each time.

As previously indicated, a 5-HT re-uptake inhibitor, preferably sertraline, in combination with compounds of formula I are readily adapted to therapeutic use as antidepressant agents. In general, these antidepressant compositions containing a 5-HT re-uptake inhibitor, preferably sertraline, and a compound of formula I are normally administered in dosages ranging from about 0.01 mg. to about 100 mg. per kg. of body weight per day of a 5-HT re-uptake inhibitor, preferably sertraline, preferably from about 0.1 mg. to about 10 mg. per kg. of body weight per day of sertraline; with from about 0.001 mg. to about 100 mg. per kg. of body weight per day of a compound of formula I, preferably from about 0.01 mg. to about 10 mg. per kg. of body weight per day of a compound of formula I, although variations will necessarily occur depending upon the conditions of the subject being treated and the particular route of administration chosen.

The following Examples illustrate the preparation of the compounds of the present invention. Melting points are uncorrected. NMR data are reported in parts per million ($\delta$) and are referenced to the deuterium lock signal from the sample solvent (deuteriochloroform unless otherwise specified). Specific rotations were measured at room temperature using the sodium D line (589 nm). Commercial reagents were utilized without further purification. THF refers to tetrahydrofuran. DMF refers to N,N-dimethylformamide. Chromatography refers to column chromatography performed using 32–63$\mu$m silica gel and executed under nitrogen pressure (flash chromatography) conditions. Room or ambient temperature refers to 20–25° C. All non-aqueous reactions were run under a nitrogen atmosphere for convenience and to maximize yields. Concentration at reduced pressure implies the use of a rotary evaporator.

EXAMPLE 1

1-Methyl-4-[7-(5-phenyl-[1,2,4]oxadiazol-3-ylmethyoxy)-naphthalen-1-yl]-piperazine Dihydrochloride Dihydrate To a solution of 80 mg (3.33 mmol) of oil free sodium hydride in 2.0 mL of anhydrous N,N-dimethylformamide (DMF) was added 400 mg (1.65 mmol) of 1-(7-hydroxynaphthyl)-4-methylpiperazine in 4.0 mL of DMF. After stirring at room temperature for 20 min, a solution of 380 mg (1.95 mmol) of the reactant 5-chloromethyl-3-phenyl-1,2,4-oxadiazole in 2.0 mL of DMF was added and the mixture was heated at 90° C. for 16 hr. The reaction was then cooled to room temperature and poured into approximately 50 ml of $H_2O$. After stirring for 20 min, the product was extracted into diethyl ether, which was washed with $H_2O$, dried over $MgSO_4$ and evaporated to a red oil. Chromatography on silica gel, using methanol/concentrated ammonium hydroxide/methylene chloride ($CH_3OH$:conc. $NH_4OH$: $CH_2Cl_2$) (2.5:0.5:97) gave the pure free base as a light yellow oil. The oil was dissolved in ethyl acetate and treated with hydrogen chloride gas (HCl) saturated ethyl acetate which, after standing for approximately 30 min, precipitated the title product as a colorless solid, 311 mg (47%), M.p. 82° C.

$^1$H-NMR ($CDCl_3$, free base) $\delta$2.5 (s, 3H), 2.7 (bs, 4H), 3.1 (bs, 4H), 5.2 (s, 2H), 6.5 (d, 1H), 7.1 (dd, 1H), 7.2–7.6 (m, 9H), 7.7 (d, 1H).

Mass Spectrum (m/e, %): 401 ($m^{+1}$, 100), 373(5), 272, 255, 243.

Analysis calculated for $C_{24}H_{24}N_4O_2.2HCl.2H_2O$: C, 56.58; H, 5.94; N, 11.00. Found: C, 56.36; H, 6.21; N, 10.87.

By a method similar to Example 1 except that the reactant is different, the following compounds of Examples 2–40 were similarly prepared:

EXAMPLE 2

1-Methyl-4-[7-(1-phenyl-1H-tetrazol-5-yloxy)-naphthalen-1-yl]-piperazine Dihydrochloride Mp 219° C. (dec).

$^1$H NMR ($CDCl_3$) $\delta$ 2.4 (s, 3H), 2.7 (bs, 4H), 3.2 (bs, 4H), 7.2 (d, 1H), 7.4 (m, 2H), 7.6 (m, 4H), 7.9 (m, 3H), 8.3 (d, 1H).

Mass spectrum: m/e 387 ($M^{+1}$).

Analysis calculated for $C_{22}H_{22}N_5O.2HCl$: C, 57.52; H, 5.27; N, 18.29. Found: C, 57.78; H, 5.72; N, 18.40.

EXAMPLE 3

1-Methyl-4-{7-[5-(3-trifluoromethylphenyl)-[1,2,4]oxadiazol-3-ylmethoxy]-naphthalen-1-yl}-piperazine Dihydrochloride MP 175° C. (dec).

$^1$H NMR (CDCl$_3$) δ 2.4 (s, 3H), 2.8 (bs, 4H), 3.2 (bs, 4H), 5.5 (s, 2H), 7.1 (d, 1H), 7.3 (m, 2H), 7.5 (d, 1H), 7.7 (t, 2H), 7.8 (d, 1H), 7.9 (d, 1H), 8.3 (d, 1H), 8.5 (d, 1H).

Mass spectrum: m/e 387 ($M^{+1}$).

Analysis calculated for $C_{25}H_{23}F_3N_4O_2.2HCl.H_2O$: C, 53.67; H, 4.87; N, 10.02. Found: C, 53.64; H, 5.27; N, 9.86.

EXAMPLE 4

1-{7-[5-(3-Methoxyphenyl)-[1,2,4]oxadiazol-3-ylmethoxy]-naphthalen-1-yl}-4-methylpiperazine Dihydrochloride Hydrate Mp 174° C. (dec).

$^1$H NMR (CDCl$_3$) δ 2.5 (s, 3H), 2.7 (bs, 4H), 3.2 (bs, 4H), 4.0 (s, 3H), 5.5 (s, 2H), 7.1 (m, 2H), 7.3 (m, 2H), 7.5 (m, 2H), 7.7 (m, 2H), 7.9 (d, 2H).

Mass spectrum: m/e 432 ($M^{+2}$).

Analysis calculated for $C_{25}H_{26}N_4O_3.2HCl.H_2O$: C, 57.58; H, 5.80, N, 10.75. Found: C, 58.03; H, 6.20; N, 10.78.

EXAMPLE 5

1-{7-[5-(3,5-Dimethylisoxazolyl)-[1,2,4]oxadiazol-3-ylmethoxy]-naphthalen-1-yl}-4-methylpiperazine Dihydrochloride Hydrate Mp 222–223° C.

$^1$H NMR (CDCl$_3$) δ 2.5 (s, 3H), 2.6 (s, 3H), 2.7 (bs, 4H), 2.8 (s, 3H), 3.2 (bs, 4H), 5.5 (s, 2H), 7.1 (d, 1H), 7.4 (m, 2H), 7.5 (d, 1H), 7.7 (d, 1H), 7.8 (d, 1H).

Mass spectrum: m/e 420 ($M^{+1}$).

Analysis calculated for $C_{23}H_{25}N_5O_3.2HCl.H_2O$: C, 54.12; H, 5.73, N, 13.72. ound: C, 53.75; H, 6.02; N, 13.66.

EXAMPLE 6

1-{7-[5-(2-Methoxyphenyl)-[1,2,4]oxadiazol-3-ylmethoxy]-naphthalen-1-yl}-4-methylpiperazine Dihydrochloride Hydrate Mp 186° C. (dec).

$^1$H NMR (CDCl$_3$) δ 2.5 (s, 3H), 2.7 (bs, 4H), 3.2 (bs, 4H), 4.0 (s, 3H), 5.5 (s, 2H), 7.1 (m, 3H), 7.3 (m, 2H), 7.5 (m, 2H), 7.7 (d, 1H), 7.8 (d, 1H), 8.1 (bs, 1H).

Mass spectrum: m/e 432 ($M^{+2}$).

Analysis calculated for $C_{25}H_{25}N_4O_3.2HCl.H_2O$: C, 57.58; H, 5.80, N, 10.75. Found: C, 57.67; H, 5.95; N, 10.72.

EXAMPLE 7

1-[7-(5-Tert-butyl-[1,2,4]oxadiazol-3-ylmethoxy)-naphthalen-1-yl]-4-methylpiperazine Hydrochloride Dihydrate Mp 85° C. (dec).

$^1$H NMR (CDCl$_3$) δ 1.5 (s, 9H), 2.5 (s, 3H), 2.8 (bs, 4H), 3.2 (bs, 4H), 5.4 (s, 2H), 7.1 (d, 1H), 7.3 (m, 2H), 7.5 (d, 1H), 7.7 (d, 1H), 7.8 (d, 1H).

Mass spectrum: m/e 381 ($M^{+1}$).

Analysis calculated for $C_{22}H_{28}N_4O_2.HCl.2H_2O$: C, 58.33; H, 7.34, N, 12.37. Found: C, 58.52; H, 7.18; N, 12.39.

EXAMPLE 8

1-Methyl-4-[7-(3-phenyl-[1,2,4]oxadiazol-5-ylmethoxy)-naphthalen-1-yl]-piperazine Dihydrochloride Hemihydrate Mp 160° C. (dec).

$^1$H NMR (CDCl$_3$) δ 2.4 (s, 3H), 2.7 (bs, 4H), 3.2 (bs, 4H), 5.6 (s, 2H), 7.1 (d, 1H), 7.3 (m, 2H), 7.5 (m, 4 H), 7.6 (d, 1H), 7.8 (d, 1H), 8.2 (m, 2H).

Mass spectrum: m/e 401 ($M^{+1}$).

Analysis calculated for $C_{24}H_{24}N_4O_2.2HCl.0.5H_2O$: C, 59.75; H, 5.64, N, 11.61. Found: C, 59.50; H, 5.70; N, 11.47.

EXAMPLE 9

1-{7-[5-(4-Methoxyphenyl)-[1,2,4]oxadiazol-3-ylmethoxy]-naphthalen-1-yl}-4-methylpiperazine Dihydrochloride Hydrate Mp 149° C. (dec), $^1$H NMR (CDCl$_3$) δ 2.5 (s, 3H), 2.7 (bs, 4H), 3.2 (bs, 4H), 3.9 (s, 3H), 5.4 (s, 2H), 7.0 (d, 2H), 7.1 (d, 1H), 7.25 (m, 2H), 7.5 (d, 1H), 7.65 (d, 1H), 7.7 (d, 1H), 8.1 (d, 2H).

Mass spectrum: m/e 431 ($M^{+1}$).

Analysis calculated for $C_{25}H_{26}N_4O_3.2HCl.1.5H_2O$: C, 56.60; H, 5.89, N, 10.56. Found: C, 56.30; H, 5.76; N, 10.28.

EXAMPLE 10

1-{7-[5-(4-Chlorophenyl)-[1,2,4]oxadiazol-3-ylmethoxy]-naphthalen-1-yl}-4-methylpiperazine Dihydrochloride Dihydrate Mp 186° C. (dec).

$^1$H NMR (CDCl$_3$) δ 2.5 (s, 3H), 2.7 (bs, 4H), 3.2 (bs, 4H), 5.4 (s, 2H), 7.05 (d, 1H), 7.25 (m, 2H), 7.5 (d, 3H), 7.65 (d, 1H), 7.7 (d, 2H), 8.1 (d, 2H).

Mass spectrum: m/e 435 ($M^{+1}$).

Analysis calculated for $C_{24}H_{23}N_4O_2.2HCl.2H_2O$: C, 53.00; H, 5.37, N, 10.30. Found: C, 52.95; H, 5.05; N, 10.22.

EXAMPLE 11

1-{7-[5-(2,4-Dichlorobenzyl)-[1,2,4]oxadiazol-3-ylmethoxy]-naphthalen-1-yl}-4-ethylpiperazine Dihydrochloride Hydrate Mp 90° C. (dec).

$^1$H NMR (CDCl$_3$) δ 2.5 (s, 3H), 2.7 (bs, 4H), 3.1 (bs, 4H), 5.3 (s, 2H), 5.4 (s, 2H), 6.8 (m, 1H), 7.1 (m, 2H), 7.3 (m, 2H), 7.4 (d, 1H), 7.5 (d, 1H), 7.6 (d, 1H), 7.7 (d, 1H).

Mass spectrum: m/e 499 ($M^{+NH_3}$).

Analysis calculated for $C_{25}H_{24}N_4O_3Cl_2.2HCl.H_2O$: C, 50.86; H, 4.78, N, 9.49. Found: C, 51.24; H, 4.70; N, 9.38.

EXAMPLE 12

1-{7-[3-(4-Chlorobenzyl)-[1,2,4]oxadiazol-5-ylmethoxy]-naphthalen-1-yl}-4-methylpiperazine Dihydrochloride Hemihydrate Mp 118° C. (dec)

$^1$H NMR (CDCl$_3$) δ 2.5 (s, 3H), 2.7 (bs, 4H), 3.1 (bs, 4H), 4.1 (s, 2H), 5.4 (s, 2H), 7.1 (d, 1H), 7.15–7.4 (m, 6H), 7.5 (d, 1H), 7.6 (d, 1H), 7.7 (d, 1H).

Mass spectrum: m/e 449 (M$^{+1}$).

Analysis calculated for $C_{25}H_{25}ClN_4O_2 \cdot 2HCl \cdot 0.5H_2O$: C, 56.56; H, 5.32, N, 10.55. Found: C, 56.89; H, 5.24; N. 10.56.

EXAMPLE 13

5-Chloro-2-[8-(4-methylpiperazin-1-yl)-naphthalen-2-yloxymethyl]-benzooxazole Dihydrochloride Mp 195° C. (dec).

$^1$H NMR (CDCl$_3$) δ 2.5 (s, 3H), 2.7 (bs, 4H), 3.1 (bs, 4H), 5.5 (s, 2H), 7.1 (d, 1H), 7.2–7.4 (m, 3H), 7.5 (m, 2H), 7.6–7.8 (m, 3H).

Mass spectrum: m/e 408 (M$^{+1}$).

Analysis calculated for $C_{23}H_{22}ClN_3O_2 \cdot 2HCl$: C, 57.45; H, 5.03, N, 8.74. Found: C, 57.11; H, 5.10; N, 8.69.

EXAMPLE 14

2-[8-(4-Methylpiperazin-1-yl)-naphthalen-2-yloxymethyl]-5-trifluoro-methylbenzothiazole Dihydrochloride Dihydrate Mp 179° C. (dec).

$^1$H NMR (CDCl$_3$) δ 2.5 (s, 3H), 2.6 (bs, 4H), 3.1 (bs, 4H), 5.2 (s, 2H), 7.0 (d, 1H), 7.2 (m, 2H), 7.5 (d, 1H), 7.6 (m, 2H), 7.7 (d, 1H), 8.0 (d, 1H), 8.3 (s, 1H).

Mass spectrum: m/e 458 (M$^{+1}$).

Analysis calculated for $C_{24}H_{22}F_3N_3OS \cdot 2HCl \cdot 2H_2O$: C, 46.10; H, 4.64, N, 6.45. Found: C, 46.56; H, 4.70; N, 6.55.

EXAMPLE 15

1-{7-[3-(4-Methoxyphenyl)-[1,2,4]oxadiazol-5-ylmethoxy]-naphthalen-1-yl}-4-methylpiperazine Dihydrochloride Hemihydrate Mp 184° C. (dec).

$^1$H NMR (CDCl$_3$) δ 2.4 (s, 3H), 2.7 (bs, 4H), 3.1 (bs, 4H), 3.8 (s, 3H), 5.5 (s, 2H), 7.0 (d, 2H), 7.1 (d, 1H), 7.2 (m, 2H), 7.5 (d, 1H), 7.6 (d, 1H), 7.7 (d, 1H), 8.0 (d, 2H).

Mass spectrum: m/e 431 (M$^{+1}$).

Analysis calculated for $C_{25}H_{25}N_4O_3 \cdot 2HCl \cdot 0.5H_2O$: C, 58.59; H, 5.70, N, 10.93. Found: C, 56.68; H, 5.43; N, 10.72.

EXAMPLE 16

1-{7-[3-(2-Methoxyphenyl)-[1,2,4]oxadiazol-5-ylmethoxy]-naphthalen-1-yl}-4-methylpiperazine Dihydrochloride Hydrate Mp 206° C. (dec).

$^1$H NMR (CDCl$_3$) δ 2.4 (s, 3H), 2.7 (bs, 4H), 3.1 (bs, 4H), 3.9 (s, 3H), 5.5 (s, 2H), 7.0 (m, 3H), 7.2 (m, 2H), 7.4 (m, 2H), 7.6 (d, 1H), 7.7 (d, 1H), 8.2 (dd, 1H).

Mass spectrum: m/e 431 (M$^{+1}$).

Analysis calculated for $C_{25}H_{26}N_4O_3 \cdot 2HCl \cdot H_2O$: C, 57.58; H, 5.80, N, 10,75. Found: C, 57.70; H, 5.48; N, 10.37.

EXAMPLE 17

1-{7-[3-(4-Chlorophenyl)-[1,2,4]oxadiazol-5-ylmethoxy]-naphthalen-1-yl}-4-methylpiperazine Dihydrochloride Mp 231–232° C. (dec).

$^1$H NMR (CDCl$_3$) δ 2.4 (s, 3H), 2.7 (bs, 4H), 3.2 (bs, 4H), 5.5 (s, 2H), 7.1 (d, 1H), 7.3 (m, 2H), 7.5 (m, 2H), 7.6 (d, 1H), 7.7 (d, 1H), 8.0 (d, 2H).

Mass spectrum: m/e 435 (M$^{+1}$).

Analysis calculated for $C_{24}H_{23}ClN_4O_2 \cdot 2HCl$: C, 56.76; H, 4.96, N, 11.03. Found: 56.36; H, 4.88; N, 10.78.

EXAMPLE 18

1-{7-[5-(2-Methoxyphenyl)-[1,2,4]oxadiazol-3-ylmethoxymethyl]-naphthalen-1-yl}-4-methylpiperazine Dihydrochloride Hydrate Mp 135° C. (dec).

$^1$H NMR (CDCl$_3$) δ 2.5 (s, 3H), 2.7 (bs, 4H), 3.2 (bs, 4H), 4.0 (s, 3H), 4.9 (s, 2H), 5.0 (s, 2H), 7.1 (m, 3H), 7.4 (t, 1H), 7.5 (m, 3H), 8.1 (dd, 1H), 8.2 (s, 1H).

Mass spectrum: m/e 444 (M$^{+1}$).

Analysis calculated for $C_{26}H_{28}N_4O_3 \cdot 2HCl \cdot 1.5H_2O$: C, 57.35; H, 6.11, N, 10.29. Found: C, 57.31; H, 6.20; N, 10.20.

EXAMPLE 19

1-(7-{1-[5-(4-Chlorophenyl)-[1,3,4]oxadiazol-2-yl]ethoxy}-naphthalen-1-yl)-4-methylpiperazine Hydrochloride Dihydrate Mp 65° C. (dec).

$^1$H NMR (CDCl$_3$) δ 2.0 (d, 3H), 2.5 (s, 3H), 2.7 (bs, 4H), 3.2 (m, 4H), 5.9 (q, 1H), 7.1 (d, 1H), 7.2–7.4 (m, 2H), 7.5 (m, 3H), 7.7 (d, 1H), 7.75 (d, 1H), 8.0 (d, 2H).

Mass spectrum: m/e 449 (M$^{+1}$).

Analysis calculated for $C_{25}H_{25}ClN_4O_2 \cdot HCl \cdot 2H_2O$: C, 57.58; H, 5.80, N, 10.74. Found: C, 58.15; H, 5.99; N, 10.52.

EXAMPLE 20

1-{7-[3-(2-Fluorophenyl)-[1,2,4]oxadiazol-5-ylmethoxy]-naphthalen-1-yl}-4-methylpiperazine Dihydrochloride Mp 144° C.

$^1$H NMR (CDCl$_3$) δ 2.4 (s, 3H), 2.74 (bs, 4H), 3.09 (bs, 4H), 5.54 (s, 2H), 7.12 (dd, 1H), 7.21–7.35 (m, 4H), 7.51 (m, 2H), 7.60 (d, 1H), 7.79 (d, 1H), 8.08 (t, 1H).

Mass spectrum: m/e 419 (M$^{+1}$).

Analysis calculated for $C_{24}H_{23}FN_4O_2 \cdot 2HCl \cdot 1H_2O$: C, 56.58;H, 5.34; N, 11.00. Found: C, 56.71; H, 5.40; N, 10.86.

EXAMPLE 21

5-Bromo-2-[8-(4-methylpiperazin-1-yl)-naphthalen-2-yloxymethyl]-benzooxazole Dihydrochloride Mp 182° C. (dec).

$^1$H NMR (CDCl$_3$) δ 2.44 (s, 3H), 2.67 (bs, 4H), 3.07 (bs, 4H), 5.48 (s, 2H), 7.11 (dd, 1H), 7.29 (m, 2H), 7.41–7.52 (m, 3H), 7.66 (d, 1H), 7.77 (d, 1H), 7.89 (d, 1H).

Mass spectrum: m/e 452 (M$^{+1}$).

Analysis calculated for $C_{23}H_{22}BrN_3O_2 \cdot 2HCl \cdot 0.5H_2O$: C, 51.70; H, 4.72; N, 7.86. Found: C, 52.07; H, 4.62; N, 7.74.

EXAMPLE 22

6-Fluoro-2-[8-(4-methylpiperazin-1-yl)-naphthalen-2-yloxymethyl]-benzooxazole Dihydrochloride Mp 175° C. (dec).

$^1$H NMR (CDCl$_3$) δ 2.44 (s, 3H), 2.70 (bs, 4H), 3.08 (bs, 4H), 5.47 (s, 2H), 7.12 (m, 2H), 7.25–7.33 (m, 3H), 7.51 (d, 1H), 7.68 (m, 2H), 7.78 (d, 1H).

Mass spectrum: m/e 392 (M$^{+1}$).

EXAMPLE 23

6-Methoxy-2-[8-(4-methylpiperazin-1-yl)-naphthalen-2-yloxymethyl]-benzothiazole Dihydrochloride Mp 191° C. (dec).

$^1$H NMR (CDCl$_3$) δ 2.42 (s, 3H), 2.63 (bs, 4H), 3.03 (bs, 4H), 3.87 (s, 3H), 5.61 (s, 2H), 7.10 (m, 2H), 7.25–7.33 (m, 3H), 7.50 (d, 1H), 7.63 (d, 1H), 7.78 (d, 1H), 7.93 d, 1H).

Mass spectrum: m/e 420 (M+$^1$).

Analysis calculated for C$_{24}$H$_{22}$BrN$_3$O$_2$S.3HCl.3H$_2$O: C, 49.45; H, 5.88; N, 7.21. Found: C, 49.75; H, 5.83; N, 7.02.

EXAMPLE 24

2-[8-(4-Methylpiperazin-1-yl)-naphthalen-2-yloxy]-pyrimidine

Mp 150–152° C. (dec).

$^1$H NMR (CDCl$_3$) δ 2.33 (s, 3H), 2.61 (bs, 4H), 3.08 (bs, 4H), 6.95 (t, 1H), 7.06 (d, 1H), 7.30 (m, 2H), 7.50 (d, 1H), 7.82 (d, 1H), 8.00 (s, 1H), 8.48 (d, 2H).

HRMS calculated for C$_{19}$H$_{20}$N$_4$O: 320.1642. Found: 320.16536.

EXAMPLE 25

2-[8-(4-Methylpiperazin-1-yl)-naphthalen-2-yloxy]-5-trifluoromethyl-pyrimidine

Mp 84–86° C. (dec).

$^1$H NMR (CDCl$_3$) δ 2.37 (s, 3H), 2.65 (bs, 4H), 3.12 (bs, 4H), 7.03 (d, 1H), 7.13 (d, 1H), 7.25 (dd, 1H), 7.40 (t, 1H), 7.56 (d, 1 H), 7.88 (d, 1H), 7.95 (d, 1H), 8.45 (d, 1H).

Mass spectrum: m/e 388 (M$^{+1}$).

EXAMPLE 26

5-Fluoro-2-[8-(4-methylpiperazin-1-yl)-naphthalen-2-yloxy]-pyrimidine $^1$H NMR (CDCl$_3$) δ 2.45 (s, 3H), 2.70 (bs, 4H), 3.15 (bs, 4H), 7.12 (d, 1H), 7.20 (dd, 1H), 7.30 (dd, 1H), 7.40 (t, 1H), 7.55 (t, 1H), 7.80–7.95 (m, 2H), 8.00 (d, 1H), 8.45 (s, 1H).

EXAMPLE 27

2-[8-(4-Methylpiperazin-1-yl)-naphtha)en-2-yloxymethyl]-quinoline $^1$H NMR (CDCl$_3$) δ 2.3 (s, 3H), 2.6 (bs, 4H), 3.2 (bs, 4H), 7.1 (m, 2H), 7.4 (m, 3H), 7.6 (m, 2H), 7.7 (m, 2H), 7.8 (d, 1H), 8.1 (d, 1H), 8.2 (d, 1H).

Mass spectrum: m/e 370 (M$^{+1}$).

HRMS calculated for C$_{24}$H$_{23}$N$_3$O: 369.1841. Found: 369.18087.

EXAMPLE 28

1-[7-(5-Chloropyridin-2-yloxy)-naphthalen-1-yl]-4-methyl-piperazine $^1$H NMR (CDCl$_3$) δ 2.38 (s, 3H), 2.65 (bs, 4H), 3.12 (bs, 4H), 6.90 (d, 1H), 7.11 (d, 1H), 7.23 (dd, 1H), 7.37 (t, 1H), 7.55 (d, 1H), 7.65 (dd, 1H), 7.84 (d, 1H), 7.90 (d, 1H), 8.12 (d, 1H).

HRMS calculated for C$_{20}$H$_{20}$ClN$_3$O: 353.1295. Found: 353.11642.

EXAMPLE 29

1-[7-(5-Chlorothiophen-2-ylmethoxy)-naphthalen-1-yl]-4-methyl-piperazine mp 83–85° C.

Mass spectrum: m/e 373 (M$^{+1}$).

$^1$H NMR (CDCl$_3$) δ 2.43 (s, 3H), 2.70 (bs, 4H), 3.10 (bs, 4H), 5.25 (s, 2H), 6.80 (d, 1H), 6.90 (d, 1H), 7.10 (d, 1H), 7.16 (dd, 1H), 7.27 (t, 1H), 7.50 (d, 1H), 7.58 (d, 1H), 7.75 (d, 1H).

EXAMPLE 30

2-[8-(4-Methylpiperazin-1-yl)-naphthalen-2-yloxy]-nicotinonitrile $^1$H NMR (CDCl$_3$) δ 2.37 (s, 3H), 2.65 (bs, 4H), 3.10 (bs, 4H), 7.05 (dd, 1H), 7.10 (d, 1H), 7.25 (dd, 1H), 7.37 (t, 1H), 7.55 (d, 1H), 7.85 (d, 1 H), 7.98 (dd, 2H), 8.25 (dd, 1H).

HRMS calculated for C$_{21}$H$_{20}$N$_4$O: 344.1637. Found: 344.16176.

EXAMPLE 31

2-[8-(4-Methylpiperazin-1-yl)-naphthalen-2-yloxymethyl]-quinoline $^1$H NMR (CDCl$_3$) δ 2.25 (s, 3H), 2.35 (bs, 4H), 2.85 (bs, 4H), 5.55 (s, 2H), 7.0 (d, 1H), 7.2 (t, 1H), 7.3 (dd, 1H), 7.45 (m, 3H), 7.6 (d, 1H), 7.7 (m, 3H), 8.05 (d, 1H), 8.15 (d, 1H).

HRMS calculated for C$_{25}$H$_{25}$N$_3$O: 383.1992. Observed: 383.19964

EXAMPLE 32

2-[8-(1-Methylpiperidin-4-yl)-naphthalen-2-yloxy]-pyrimidine

Mp 134–135° C.

$^1$H NMR (CDCl$_3$) δ 2.01 (m, 4H), 2.25 (m, 2H), 2.41 (s, 3H), 3.11 (bd, 2H), 3.21 (m, H), 7.07 (t, 1H), 7.35 (dd, 1H), 7.44 (d, 1H), 7.46 (s, 1H), 7.74 (m, 1H), 7.89 (d, 1H), 7.93 (d, 1H), 8.59 (d, 2H).

HRMS calculated for C$_{20}$H$_{21}$N$_3$O: 319.1680. Observed m/e: 319.1676.

Analysis calculated for C$_{20}$H$_{21}$N$_3$O.H$_2$O: C, 73.15; H. 6.75; N, 12.79. Found: C, 72.94; H, 6.78; N, 12.66.

EXAMPLE 33

1-Methyl-4-[7-(3-phenyl-[1,2,4]oxadiazol-5-ylmethoxy)-naphthalen-1-yl]-piperidine Mp 106–108° C.

$^1$H NMR (CDCl$_3$) δ 1.85–2.03 (m, 4H), 2.22 (m, 2H), 2.36 (s, 3H), 3.02 (bd, 2H), 3.13 (m, 1H), 5.50 (s, 2H), 7.25–7.42 (m, 3H), 7.45–7.58 (m. 4H), 7.65 (d, 1H), 7.82 (d, 1H), 8.10 (dd, 2H).

HRMS calculated for C$_{25}$H$_{25}$N$_3$O$_2$: 399.4914. Observed m/e: 399.1965

Analysis calculated for C$_{25}$H$_{25}$N$_3$O$_2$.0.25H$_2$O: C, 74.33; H, 6.36; N, 10.40. Found: C, 74.23; H, 6.42; N, 10.49.

EXAMPLE 34

1-Methyl-4-[7-(pyridin-2-ylmethoxy)-naphthalen-1-yl]-piperazine $^1$H NMR (CDCl$_3$) δ 2.38 (s, 3H), 2.60 (bs, 4H), 2.99 (bs, 4H), 5.35 (s, 2H), 7.03 (d, 1H), 7.23 (m, 3H), 7.43–7.53 (m, 3H), 7.63 (m, 1H), 7.71 (d, 1H), 8.59 (m, 1H).

HRMS calculated for $C_{21}H_{23}N_3O$: 333.1841. Observed m/e: 333.18425.

EXAMPLE 35

1-Methyl-4-[7-(3-pyridin-3-ylpropoxy)-naphthalen-1-yl]-piperazine $^1$H NMR (CDCl$_3$) δ 2.2 (q, 2H), 2.4 (s, 3H), 2.75 (bs, 4H), 2.9 (t, 2H), 3.15 (bs, 4H), 4.1 (t, 2H), 7.05–7.30 (m, 4H), 7.5 (m, 3H), 7.7 (d, 1H), 8.45 (dd, 1H), 8.52 (d, 1H).

HRMS calculated for $C_{23}H_{27}N_3O$: 361.2148. Observed m/e: 361.21118.

EXAMPLE 36

1-{7-[2-(4-Chlorophenyl)-thiazol-4-ylmethoxy]-naphthalen-1-yl}-4-methyl-piperazine $^1$H NMR (CDCl$_3$) δ 2.25 (s, 3H), 2.6 (bs, 4H), 3.05 (bs, 4H), 5.4 (s, 2H), 7.05 (d, 1H), 7.25 (m, 3H), 7.35 (m, 2H), 7.5 (d, 1H), 7.55 (d, 1H), 7.75 (d, 1H), 7.85 (d, 2H).

HRMS calculated for $C_{25}H_{24}ClN_3OS$: 449.1407. Observed m/e: 449.13387.

EXAMPLE 37

4-{7-[5-(3,5-Dimethylisoxazol-4-yl)-[1,2,4] oxadiazol-3-ylmethoxy]-naphthalen-1-yl}-1-methylpiperidine Mp 84–86° C.

$^1$H NMR (CDCl$_3$) δ 1.80–2.00 (m, 4H), 2.23 (dt, 2H), 2.39 (s, 3H), 2.59 (s, 3H), 2.81 (s, 3H), 3.06 (bd, 2H), 3.18 (m, 1H), 5.40 (s, 2H), 7.26–7.32 (m, 1H), 7.36 (d, 1H), 7.41 (dd, 1H), 7.56 (d, 1H), 7.67 (d, 1H), 7.82 (d, 1H).

HRMS calculated for $C_{24}H_{25}N_4O_3$: 418.1999. Observed m/e: 418.1996.

EXAMPLE 38

7-Chloro-2-[8-(4-methylpiperazin-1-yl)-naphthalen-2-yloxymethyl]-quinoline

Mp 246–247° C. (dec.)

$^1$H NMR (CDCl$_3$) δ 2.30 (s, 3H), 2.40 (bs, 4H), 2.86 (bs, 4H), 5.52 (s, 2H), 7.01 (d, 1H), 7.25 (m, 2H), 7.45 (m, 3H), 7.63 (m, 2H), 7.73 (d, 1H), 8.02 (d, 1H), 8.13 (d, 1H).

$^{13}$H NMR (CDCl$_3$) ppm: 46.1, 52.2, 55.5, 71.1, 103.9, 115.4, 118.7, 119.1, 123.2, 123.9, 125.8, 127.5, 128.2, 128.9, 129.8, 130.2, 130.3, 135.6, 136.6, 148.0, 148.6, 155.9, 159.7.

Mass spectrum: m/e 418 ($M^{+1}$).

EXAMPLE 39

6Chloro-5-{2-[8-(4-methylpiperazin-1-yl)-naphthalen-2-yloxy]-ethyl}-1,3-dihydro-indol-2-one Mp 93° C. (dec.).

$^1$H NMR (CDCl$_3$) δ 2.4 (s, 3H), 2.75 (bs, 4H), 3.15 (bs, 4H), 3.25 (t, 2H), 3.50 (s, 2H), 4.35 (t, 2H), 6.9 (s, 1H), 7.1 (t, 2H), 7.25 (t, 2H), 7.50 (d, 1H), 7.55 (m, 1H), 7.70 (d, 1H), 9.40 (s, 1H).

HRMS calculated for $C_{25}H_{26}ClN_3O_2$: 435.1714. Found: 435.17042.

EXAMPLE 40

3-[8-(4-Methylpiperazin-1-yl)-naphthalen-2-yloxy]-6-phenylpyridazine

Mp 158–160° C.

$^1$H NMR (CDCl$_3$) δ 2.35 (s, 3H), 2.64 (bs, 4H), 3.12 (bs, 4H), 7.11 (d, 1H), 7.23 (t, 1H), 7.33–7.46 (m, 5H), 7.55 (d, 1H), 7.85 (m, 2H), 8.00 (m, 3H).

Mass spectrum: m/e 397 ($M^{+1}$).

According to the methods of U.S. patent application Ser. No. 08/032,042 now abandoned and PCT Application No. PCT/US 94/01206. The following examples were prepared.

EXAMPLE 41

8-(4-Methylpiperazin-1-yl)-naphthalen-2-carboxylic Acid [1-(4-chlorophenyl)ethyl]-amide Mp 152.5–153° C.

$^1$H NMR (CDCl$_3$) δ 1.65 (d,3H), 2.45 (s, 3H), 2.75 (bs, 4H), 3.20 (bs, 4H), 5.38 (m, 1H), 6.45 (d, 1H), 7.15 (dd, 1H), 7.27 (s, 1H), 7.40 (m, 3H), 7.50 (t, 1H), 7.60 (d, 1H), 7.75 (dd, 1H), 7.90 (d, 1H), 8.75 (s, 1H).

Mass spectrum: m/e 407 ($M^+$).

EXAMPLE 42

8-(4-Methylpiperazin-1-yl)-naphthalene-2-carboxylic acid [3-(4-chlorophenyl)propyl]-amide Mp 121.5–123° C.

$^1$H NMR (CDCl$_3$) δ 2.05 (m, 2H), 2.45 (s, 2H), 2.75 (m, 6H), 3.20 (bs, 4H), 3.55 (m, 2H), 6.35 (bs, 1H), 7.10–7.35 (m, 5H), 7.48 (m, 1H), 7.55 (d, 1H), 7.68 (m, 1H), 7.85 (dd, 1H), 8.68 (bs, 1H).

Mass spectrum: m/e 421 ($M^+$).

EXAMPLE 43

8-(Piperazin-1-yl)-naphthalene-2-carboxylic acid 4-chlorobenzamide $^1$H NMR (CDCl$_3$) δ 1.78 (s, 1H), 3.05 (m, 9H), 4.60 (d, 2H), 6.85 (t,1H), 7.07 (dd, 1H), 7.23 (m, 3H), 7.45 (m, 2H), 7.74 (m, 2H), 8.65 (s, 1H).

EXAMPLE 44

8-(4-Methylpiperazin-1-yl)-naphthalene-2-carboxylic Acid (4-chloro-benzyl)-methylamide Dihydrochloride $^1$H NMR (CDCl$_3$, free base) δ 2.7 (s, 1H), 2.95–3.80 (m, 13H), 4.07 (d, 1H), 4.7 (d, 1H), 7.2–7.65 (m, 7H), 7.75 (d, 1H), 7.95 (d, 1H), 8.25 (d, 1H).

Mass spectrum: m/e 407 ($M^+$).

EXAMPLE 45

8-(4-Methylpiperazin-1-yl)-naphthalene-2-carboxylic Acid [2-(4-chlorophenyl)ethyl]-amide Mp 122–123° C.

$^1$H NMR (CDCl$_3$) δ 2.45 (s, 3H), 2.77 (bs, 4H), 2.95 (t, 2H), 3.12 (bs, 4H), 3.32 (m, 1H), 3.68 (t, 2H), 7.17 (dd, 1H), 7.30 (m, 4H), 7.50 (t, 1H), 7.60 (d, 1H), 7.80 (dd, 1H), 7.90 (d, 1H), 8.62 (d, 1H).

Mass spectrum: m/e 408 ($M^{+1}$).

EXAMPLE 46

8-(4-Methylpiperazin-1-yl)-naphthalene-2-carboxylic Acid Pyrimidin-4-ylamide $^1$H NMR (CDCl$_3$) δ 2.36 (s, 3H), 2.70 (bs, 4H), 3.10 (bs, 4H), 7.15 (dd, 1H), 7.55 (q+t, 2H), 7.91 (d, 1H), 8.41 (dd, 1H), 8.65 (d, 1H), 8.73 (d, 1H), 8.82 (s, 1H), 9.48 (s, 1H).

HRMS calculated for $C_{20}H_{21}N_5O$: 347.1742. Found: 347.16974.

The compounds of Examples 47–50 were prepared from the intermediates of Preparation 5.

EXAMPLE 47

1-(1-Methylpiperidin-4-yl)-7-naphthalene Carboxylic Acid 3-phenylpropylamide A mixture of 1-(1-methylpiperidin-4-yl)-7-trifluoromethanesulfonyloxynaphthalene (0.25 g, 0.67 mmol), triethylamine (0.373 mL, 2.68 mmol), 3-phenylpropylamine (0.286 mL, 2.01 mmol), and bis-(triphenylphosphine)palladium chloride (0.025 g, 0.033 mmol) was blanketed with an atmosphere of carbon monoxide (balloon) and heated to 105° C. for 16 h. The reaction was diluted with ethyl acetate and filtered through celite. The filtrate was washed with water and brine, dried and concentrated. The residue was flash chromatographed on silica gel (1×3 inches packed with 75% ethyl acetate/hexane). Elution proceeded as follows: 75% ethyl acetate/hexane, 150 mL, nil; ethyl acetate, 150 mL, nil; 2% methanol/1% triethylamine/ethyl acetate, 200 mL and 2% methanol/1% triethylamine/ethyl acetate, 100 mL, 0.21 g of an oil. Bulb to bulb distillation removed impurities (pot temperature up to 120° C., 1 mm mercury (Hg)). The pot residue was pure product and weighed 0.190 g (73%). The 1-(1-methylpiperidin-4-yl)-7-naphthalene carboxylic acid 3-phenylpropyl amide obtained in this manner solidified on standing and had mp 47–50° C.; $^1$H NMR (250 MHz, CDCl$_3$) δ 8.67 (s, 1 H), 7.86 (d, J=8.5 Hz, 1 H), 7.73 (d, J=6.5 Hz, 1 H), 7.61–7.43 (m, 3 H), 7.36–7.18 (m, 5 H), 6.33 (br s, 1 H), 3.58 (q, J=6.5 Hz, 2 H), 3.42 (sym m, 1 H), 3.05 (br d, J=11.5 Hz, 2 H), 2.77 (t, J=7.5Hz, 2 H), 2.38 (s, 3 H), 2.27 (sym m, 2 H), 2.10–1.88 (m, 6 H).

Analysis calculated for $C_{26}H_{30}N_2O.0.75$ $H_2O$: C, 78.06; H, 7.94; N, 7.00. Found: C, 77.92; H, 7.91; N, 6.70.

EXAMPLE 48

1-(1-Methylpiperidin-4-yl)-7-naphthalenecarboxylicacid3-(4-chlorophenyl)propyl Amide A mixture of 1-(1-methylpiperidin-4-yl)-7-trifluoromethanesulfonyloxynaphthalene (0.25 g, 0.67 mmol), triethylamine (0.373 mL, 2.68 mmol), 3-(4-chlorophenyl)propylamine (0.341 mL, 2.01 mmol), and bis-(triphenylphosphine)palladium chloride (0.025 g, 0.033 mmol) was blanketed with an atmosphere of carbon monoxide (balloon) and heated to 105° C. for 16 hours(h). The reaction was diluted with ethyl acetate and filtered through celite. The filtrate was washed with water and brine, dried and concentrated. The residue was flash chromatographed on silica gel (1×3 inches packed with 75% ethyl acetate/hexane). Elution proceeded as follows: 75% ethyl acetate/hexane, 150 mL, nil; ethyl acetate, 150 mL, nil; 2% methanol/1% triethylamine/ethyl acetate, 200 mL and 2% methanol/1% triethylamine/ethyl acetate, 150 mL, 0.196 g of a yellow oil which slowly crystallized. This material was recrystallized from chloroform/ether to give 0.064 g (23%) of 1-(1-methylpiperidin-4-yl)-7-naphthalene carboxylic acid 3-(4-chlorophenyl)propyl amide as white crystals which had mp 132–133.5° C.; $^1$H NMR (250 MHz, CDCl$_3$) δ 8.66 (s, 1 H), 7.87 (d, J=8.5 Hz, 1 H), 7.72 (d, J=7.5 Hz, 1 H), 7.58–7.46 (m, 3 H), 7.27–7.23 (m, 2 H partially obscured by the NMR solvent), 7.15 (long range coupled d, J=8.5 Hz, 2 H), 6.23 (br t, 1 H), 3.55 (q, J=6.5 Hz, 2 H), 3.39 (sym m, 1 H), 3.02 (br d, J=12 Hz, 2 H), 2.72 (t, J=7.5 Hz, 2 H), 2.36 (s, 3 H), 2.23 (sym m, 2 H), 2.04–1.89 (m, 6 H). Analysis calculated for $C_{26}H_{29}ClN_2O.0.25$ $H_2O$: C, 73.40; H, 6.99; N, 6.58. Found: C, 73.30; H, 7.12; N, 6.56.

EXAMPLE 49

1-(1-Methylpiperidin-4-yl)-7-pyrimid-5-yl)-naphthalene

A mixture of 1-(1-methylpiperidin-4-yl)-7-trifluoromethanesulfonyloxynaphthalene (0.304 g, 0.819 mmol), 5-trimethylstannylpyrimidine (0.220 g, 0.905 mmol), triethylamine (0.55 mL, 3.95 mmol), lithium chloride (0.107 g, 2.53 mmol), bis(triphenylphosphine) palladium chloride (0.029 g, 0.041 mmol), and butylated hydroxytoluene (BHT, approx. 0.01 g, antioxidant) in dimethylformamide (15 mL) was heated to 115° C. for 1 hour. The reaction was cooled and diluted with ethyl acetate. The mixture was extracted with a mixture of 1 N lithium chloride (25 mL) and 1 N sodium hydroxide (3 mL), 1 N lithium chloride and brine. The organic phase was dried over calcium sulfate and concentrated. The residue was flash chromatographed on silica gel (1×2.5 inches packed with 75% ethyl acetate/hexane). Elution proceeded as follows: 75% ethyl acetate/hexane, 225 mL, nil; ethyl acetate, 200 mL, nil; 1% methanol/ethyl acetate, 200 mL, nil; 5% methanol/ethyl acetate, 300 mL, nil; and 7% methanol/1% triethylamine/ethyl acetate, 250 mL, 0.130 g (52%) of 1-(1-methylpiperidin-4-yl)-7-pyrimid-5-yl-naphthalene as a tan foam. A sample triturated with ether afforded white crystals which had: Mp 121.5–123° C.; $^1$H NMR (250 MHz, CDCl$_3$) δ 9.27 (s, 1 H), 9.08 (s, 2 H), 8.26 (s, 1 H), 8.03 (d, J=8.5 Hz, 1 H), 7.78 (dd, J=3, 6.5 Hz, 1 H), 7.69 (dd, J=1.5, 8.5 Hz, 1 H), 7.57–7.50 (m, 2 H), 3.36 (sym m, 1 H), 3.09 (br d, J=12 Hz, 2 H), 2.40 (s, 3 H), 2.28 (sym m, 2 H), 2.06–1.90 (m, 4 H). Analysis calculated for $C_{20}H_{21}N_3$: C, 79.17; H, 6.98; N, 13.85. Found: C, 78.46; H, 7.14; N, 13.89. HRMS m/e 303.1731. Observed m/e 303.1700.

EXAMPLE 50

1-(1-Methypiperidin-4-yl)-7-(3-methoxyphenyl)-naphthalene

A mixture of 1-(1-methylpiperidin-4-yl)-7-trifluoromethanesulfonyloxynaphthalene (0.264 g, 0.712 mmol), 3-trimethylstannylanisole (0.212 g, 0.783 mmol), triethylamine (0.476 mL, 3.42 mmol), lithium chloride (0.093 g, 2.21 mmol), bis-(triphenylphosphine)palladium chloride (0.025 g, 0.036 mmol), and butylated hydroxytoluene (BHT, ⁻0.01 g, antioxidant) in dimethylformamide (12.5 mL) was heated to 115° C. for 2 h. The reaction was cooled and diluted with ethyl acetate. The mixture was extracted with a mixture of 1 N lithium chloride (25 mL) and 1 N sodium hydroxide (3 mL), 1 N lithium chloride and brine. The organic phase was dried over calcium sulfate and concentrated. The residue was flash chromatographed on silica gel (1×2.5 inches packed with 75% ethyl acetate/hexane). Elution proceeded as follows: 75% ethyl acetate/hexane, 300 mL, nil; ethyl acetate, 200 mL, 0.104 g of a yellow oil. The oil was distilled (bulb to bulb) collecting three fractions: 25–143° C. (1 mm Hg), 0.037 g identified as 1-(1-methylpiperidin4-yl)-7-methylnaphthalene; 143–168° C. (1 mm Hg), 0.008 g of a mixed fraction; 168–200° C., 0.049 g (21%) of 1-(1-methylpiperidin4-yl)-7-(3-methoxyphenyl)-naphthalene as a clear yellow oil which had $^1$H NMR (250 MHz, CDCl$_3$) δ 8.26 (s, 1 H), 7.94 (d, J=8.5

Hz, 1 H), 7.77–7.70 (m, 2 H), 7.47–7.40 (m, 3 H), 7.32 (d, J=7.5 Hz, 1 H), 7.27–7.25 m, 1 H partially obscured by the $^1$H NMR solvent), 6.96 (dd, J=2.5, 8.5 Hz, 1 H), 3.92 (s, 3 H), 3.38 (sym m, 1 H), 3.07 (br d, J=11.5 Hz, 2 H), 2.39 (s, 3 H), 2.25 (dt, J=3.5, 11 Hz, 2 H), 2.08–1.89 (m, 4 H). The product was dissolved in chloroform and HCl (gas) was bubbled into the solution. The solvent was removed and the residue was triturated with ether to afford the hydrochloride salt which had: mp 212–214° C. Analysis calculated for $C_{23}H_{25}N.HCl$: C, 75.09; H, 7.12; N, 3.81. Found: C, 75.22; H, 7.44; N, 4.19.

EXAMPLE 51

1-(1-Methylpiperidin-4-yl)-7-(pyrid-3-yl)-naphthalene

A mixture of 1-(1-methylpiperidin-4-yl)-7-trifluoromethanesulfonyloxynaphthalene (0.250 g, 0.67 mmol), 3-trimethylstannylpyridine (0.227 g, 0.94 mmol), triethylamine (0.448 mL, 3.22 mmol), lithium chloride (0.093 g, 2.21 mmol), bis-triphenylphosphine)palladium chloride (0.025 g, 0.036 mmol), and butylated hydroxytoluene (BHT, ⁻0.01 g, antioxidant) in dimethylformamide (12.5 mL) was heated 115° C. for 2.5 h. The reaction was cooled and diluted with ethyl acetate. The mixture was extracted with a mixture of 1 N lithium chloride (25 mL) and 1 N sodium hydroxide (3 mL), 1 N lithium chloride and brine. The organic phase was dried over calcium sulfate and concentrated. The residue was flash chromatographed on silica gel (1×3 inches packed with 75% ethyl acetate/hexane). Elution proceeded as follows: 75% ethyl acetate/hexane, 300 mL, nil; ethyl acetate, 200 mL, nil; 4% methanol/1% triethylamine/ethyl acetate, 300 mL, 0.091 g (45%) of 1-(1-methylpiperidin-4-yl)-7-(pyrid-3-yl)-naphthalene as a brown oil. The product was further purified by bulb to bulb distillation with the product obtained at 220° C. (1 mm Hg) as an orange oil which had: $^1$H NMR (250 MHz, CDCl$_3$) δ 8.99 (m, 1 H), 8.66 (dd, J=1.5, 5 Hz, 1 H), 8.26 (s, 1 H), 8.06–7.97 (m, 3 H), 7.81–7.76 (m, 1 H), 7.70 (dd, J=1.5, 8.5 Hz, 1 H), 7.52–7.40 (m, 3 H), 3.38 (sym m. 1 H), 3.10 (br d, J=11.5 Hz, 2 H), 2.41 (s, 3 H), 2.28 (sym m, 2 H), 2.10–1.93 (m, 4 H). The product was dissolved in chloroform and HCl (gas) was bubbled into the solution. The solvent was removed and the residue was triturated with ether to obtain 0.08 g of the hydrochloride salt as an amorphous solid which had: melting range 130–160° C. Analysis calculated for $C_{21}H_{22}N_2.2HCl.2.5\ H_2O$: C, 60.00; H, 6.95; N, 6.66. Found: C, 59.49; H, 6.85; N, 6.35.

EXAMPLE 52

General Procedure for the Synthesis of 1-(4-Methylpiperazin-1-yl)-7-(1,2,4-oxadiaz-5-yl)naphthalene To a stirred solution of sodium (2.5 equivalents) in absolute methanol (25 mL per gram sodium) at 0° C. was added hydroxylamine hydrochloride (2.5 equivalents) as a solid, and the resulting mixture was stirred at room temperature under nitrogen for 30 minutes. Then, the appropriate nitrile (1.0 equivalent) was added, and the resulting reaction mixture was heated at reflux overnight (16 hours). The reaction mixture was then cooled, filtered through Celite®, and the filtrate was evaporated under reduced pressure to afford the corresponding crude amidoxime which was used immediately and directly in the next step.

To a stirred solution of the crude amidoxime (2.0 equivalents) in anhydrous tetrahydrofuran (20 mL per gram of amidoxime) was added sodium hydride (2.2 equivalents), and the resulting reaction solution was heated at reflux under nitrogen for 30 minutes. The reaction solution was cooled, and a solution of benzyl 1-(4-methylpiperazin-1-yl) naphthalene-7-carboxylate (1.0 equivalent) in anhydrous tetrahydrofuran [10 mL per gram of benzyl 1-(4-methylpiperazin-1-yl)naphthalene-7-carboxylate] was added. The resulting reaction solution was then heated at reflux under nitrogen for two hours. The resulting reaction solution was evaporated under reduced pressure, and the residue was chromatographed using silica gel (50 g per gram residue) and elution with an appropriate solvent system to afford the corresponding 1-(4-methylpiperazin-1-yl)-7-(1,2,4-oxadiaz-5-yl)naphthalene.

Using this general procedure, the following compounds were prepared:

A. 7-(3-(4-Chlorophenylmethyl)-1,2,4-oxadiaz-5yl)-1-(4-methylpiperazin-1-yl)-naphthalene Sodium (5.6 g, 0.25 mol), hydroxylamine hydrochloride (17.3 g, 0.25 mol), and (4-chlorophenyl)acetonitrile (15.1 g, 0.10 mol) and methanol (150 mL) were used to prepare (4-chlorophenyl)acetamidoxime (18.5 g, 0.10 mol, 100%) as described above.

(4-Chlorophenyl)acetamidoxime (0.374 g, 2.00 mmol), sodium hydride (60% dispersion in oil, 0.093 g, 2.3 mmol), benzyl 1-(4-methylpiperazin-1-yl)naphthalene-7-carboxylate (0.360 g, 1.00 mmol), and anhydrous tetrahydrofuran (12 mL total) were to used form the title compound as described above. Chromatographic purification using elution with 10% methanol in ethyl acetate afforded the title compound (0.105 g, 0.25 mmol, 25%) as a off-white foam: $^{13}$C NMR (acetone-d$_6$) δ 176.7, 170.8, 150.0, 137.4, 135.8, 133.1, 131.6, 130.6, 129.7, 129.3, 128.9, 125.2, 124.9, 124.8, 121.9, 117.9, 55.2, 51.3, 44.2, 31.9; LRMS (m/z, relative intensity) 420 ([M$^+$ with $^{37}$Cl], 36), 419 (46), 418 ([M$^+$ with $^{35}$Cl], 100), 403 (14), 151 (86), 113 (77); HRMS calculated for $C_{24}H_{3}ClN_4O$ 418.1555, found 418.1543.

B. 1-(4-Methylpiperazin-1-yl)-7-(3-(pyrid-4-ylmethyl)-1,2,4-oxadiaz-5-yl)naphthalene Sodium (0.253 g, 11.5 mmol), hydroxylamine hydrochloride (0.570 g, 8.20 mmol), and (4-pyridyl)acetonitrile hydrochloride (0.500 g, 3.2 mmol) and methanol (5 mL) were used to prepare (4-pyridyl)acetamidoxime (0.580 g, >100%) as described above.

(4-Pyridyl)acetamidoxime (0.580 g, assumed 3.2 mmol), sodium hydride (60% dispersion in oil, 0.160 g, 4.0 mmol), benzyl 1-(4-methylpiperazin-1-yl)naphthalene-7-carboxylate (0.600 g, 1.66 mmol), and anhydrous tetrahydrofuran (16 mL total) were used to form the title compound as described above. Chromatographic purification using elution with 3% methanol in methylene chloride afforded the title compound (0.075 g, 0.19 mmol, 12%) as a off-white foam: $^{13}$C NMR (CD$_3$OD) δ 176.4, 168.8, 150.5, 149.0, 148.9, 146.4, 136.8, 129.4, 128.7, 128.1, 124.7, 124.6, 123.2, 122.5, 120.2, 116.1, 55.0, 52.4, 44.8, 30.9, FAB LRMS (m/z, relative intensity) 387 (32), 386 (M$^+$, 100). Anal. calcd for $C_{23}H_{23}N_5O.0.33\ NH_2OH$ [hydroxylamine]: C, 69.70; H, 6.10; N, 18.84. Found: 69.89; H, 6.00; N, 18.94.

C. 1-(4-Methylpiperazin-1-yl)-7-(3-(pyrid-3-ylmethyl)-1,2,4-oxadiaz-5-yl)naphthalene Sodium (0.183 g, 7.96 mmol), hydroxylamine hydrochloride (0.570 g, 8.20 mmol), and (3-pyridyl)acetonitrile (0.375 g, 3.17 mmol) and methanol (5 mL) were used 10 to prepare (3-pyridyl)acetamidoxime (0.50 g, >100%) as described above.

(3-Pyridyl)acetamidoxime (0.50 g, assumed 3.17 mmol), sodium hydride (60% dispersion in oil, 0.282 g, 7.0 mmol), benzyl 1-(4-methylpiperazin-1-yl)naphthalene-7-carboxylate (0.576 g, 1.60 mmol), and anhydrous tetrahydrofuran (16 mL total) were used to form the title compound as described above. Chromatographic purification using elution with 6% methanol in methylene chloride afforded the title compound (0.160 g, 0.42 mmol, 26%) as a off-white loam: $^{13}$C NMR (CD$_3$OD) δ 176.4, 169.5, 150.5, 149.2, 147.4, 137.6, 136.8, 132.5, 129.4, 128.7, 128.1, 124.5, 123.9, 123.2, 123.2, 120.3, 116.1, 55.0, 52.4, 44.7, 28.9; LRMS (m/z, relative intensity) 386 (18), 385 (M$^+$, 61), 370 (63), 342 (100), 315 (29), 287 (22), 71 (59); HRMS calculated for C$_{23}$H$_{23}$N$_5$O 0 385.1898, found 385.1906. Anal. calcd for C$_{23}$H$_{23}$N$_5$O 0.5 H$_2$O: C, 70.03; H, 6.13; N, 17.75. Found: C, 69.67; H, 6.12; N, 17.71.

D. 1-(4-Methylpiperazin-1-yl)-7-(3-(pyrid-2-ylmethyl)-1,2,4-oxadiaz-5-yl)naphthalene Sodium (0.183 g, 7.96 mmol), hydroxylamine hydrochloride (0.570 g, 8.20 mmol), and (2-pyridyl)acetonitrile (0.375 g, 3.17 mmol) and methanol (5 mL) were used to prepare (2-pyridyl)acetamidoxime (0.55 g, >100%) as described above.

(2-Pyridyl)acetamidoxime (0.55 g, assumed 3.17 mmol), sodium hydride (60% dispersion in oil, 0.282 g, 7.0 mmol), benzyl 1-(4-methylpiperazin-1-yl)naphthalene-7-carboxylate (0.576 g, 1.60 mmol), and anhydrous tetrahydrofuran (16 mL total) were used to form the title compound as described above. Chromatographic purification using elution with 6% methanol in methylene chloride afforded the title compound (0.122 g, 0.32 mmol, 20%) as a off-white foam: LRMS (m/z, relative intensity) 386 (18), 385 (M$^+$, 100), 370 (27), 182 (59), 154 (45); HRMS calculated for C$_{23}$H$_{23}$N$_5$O 385.1898, found 385.1910.

E. 7-(3-(4-Chlorophenyl)-1,2,4-oxadiaz-5-yl)-1-(4-methylpiperazin-1-yl)naphthalene Sodium (0.24 g, 10.4 mmol), hydroxylamine hydrochloride (0.70 g, 10 mmol), and 4-chlorobenzonitrile (0.548 g, 3.98 mmol) and methanol (10 mL) were used to prepare (4-chlorophenyl)amidoxime (0.70 g, 100%) as described above.

(4-Chlorophenyl)amidoxime (0.70 g, assumed 3.97 mmol), sodium hydride (60% dispersion in oil, 0.176 g, 4.4 mmol), benzyl 1-(4-methylpiperazin-1-yl)naphthalene-7-carboxylate (0.720 g, 2.0 mmol), and anhydrous tetrahydrofuran (25 mL total) were used to form the title compound as described above. Chromatographic purification using elution with 6% methanol in methylene chloride afforded the title compound (0.164 g, 0.41 mmol, 20%) as a off-white foam: $^{13}$C NMR (CDCl$_3$) δ 176.4, 168.2, 151.0, 137.5, 136.8, 129.5, 129.2, 128.9, 128.5, 125.8, 125.3, 124.0, 123.2, 120.7, 116.1, 55.5, 53.2, 46.2; LRMS (m/z, relative intensity) 406 ([M$^+$ with $^{37}$Cl], 52), 405 (45), 404 ([M$^+$ with $^{35}$Cl], 100), 319 (34), 70 (75); HRMS calculated for C$_{23}$H$_{21}$N$_4$O 404.1399, found 404.1386. Anal. calcd for C$_{23}$H$_{21}$N$_4$O: C, 68.23; H, 5.23; N, 13.84. Found: C, 68.12; H, 5.31; N, 13.96.

F. 7-(3-Methyl-1,2,4-oxadiaz-5-yl)-1-(4-methylpiperazin-1-yl)naphthalene

Sodium (0.24 g, 10.4 mmol), hydroxylamine hydrochloride (0.70 g, 10 mmol), and acetonitrile (1.2 mL, 23.0 mmol) and methanol (10 mL) were used to prepare acetamidoxime (0.80 g, >100%) as described above.

Acetamidoxime (0.80 g, assumed 10 mmol), sodium hydride (60% dispersion in oil, 0.174 g, 4.4 mmol), benzyl 1-(4-methylpiperazin-1-yl)naphthalene-7-carboxylate (0.760 g, 2.1 mmol), and anhydrous tetrahydrofuran (25 mL total) were used to form the title compound as described above. Chromatographic purification using elution with 6% methanol in methylene chloride afforded the title compound (0.120 g, 0.39 mmol, 19%) as a off-white amorphous solid: $^{13}$C NMR (CD$_3$OD) δ 177.2, 169.1, 151.9, 138.1, 130.8, 130.0, 129.5, 125.8, 124.6, 124.5, 121.8, 117.4, 56.4, 53.9, 46.2, 11.5; LRMS (m/z, relative intensity) 309 (17), 308 (M$^+$, 100), 293 (11), 223 (20), 71 (39); HRMS calculated for C$_{18}$H$_{20}$N$_4$O: 308.1633, found 308.1617. Anal. calcd for C$_{18}$H$_{20}$N$_4$O.0.25 H$_2$O: C, 69.10; H, 6.60; N, 17.91. Found: C, 69.24; H, 6.55; N, 17.79.

G. 7-(3-(4-Chlorophenoxymethyl)-1,2,4-oxadiaz-5-yl)-1-(4-methylpiperazin-1-yl)naphthalene Sodium (0.24 g, 10.4 mmol), hydroxylamine hydrochloride (0.72 g, 10 mmol), and (4-chlorophenoxy)acetonitrile (0.67 g, 4.0 mmol) and methanol (5 mL) were used to prepare (4-chlorophenoxy)acetamidoxime (0.85 g, >100%) as described above.

(4-chlorophenoxy)acetamidoxime (0.85 g, assumed 4.0 mmol), sodium hydride (60% dispersion in oil, 0.190 g, 4.7 mmol), benzyl 1-(4-methylpiperazin-1-yl)naphthalene-7-carboxylate (0.720 g, 2.0 mmol), and anhydrous tetrahydrofuran (25 mL total) were used to form the title compound as described above. Chromatographic purification using elution with ethyl acetate/methanol/triethylamine [65:1:1] afforded the title compound (0.238 g, 0.55 mmol, 27%) as a off-white foam: $^{13}$C NMR (CDCl$_3$) δ 177.0, 167.2, 156.6, 151.0, 136.8, 129.6, 129.5, 128.9, 128.4, 126.8, 125.5, 123.9, 123.3, 120.3, 116.4, 116.1, 61.6, 55.4, 53.2, 46.1; LRMS (m/z, relative intensity) 436 ([M$^+$ with $^{37}$Cl], 17), 435 (12), 434 ([M$^+$ with $^{35}$Cl, 100), 71 (97)) 70 (84); HRMS calculated for C$_{24}$H$_{23}$ClN$_4$O$_2$: 434.1504, found 434.1490. Anal. calcd for C$_{24}$H$_{23}$ClN$_4$O.0.5 H$_2$O: C, 64.93; H, 5.45; N, 12.62. Found: C, 64.74; H. 5.46; N. 12.38.

H. 7-(3-(1,1-Dimethylethyl-1,2,4-oxadiaz-5-yl)-1-(4-methylpiperazin-1-yl)naphthalene Sodium (0.112 g, 4.9 mmol), hydroxylamine hydrochloride (0.35 g, 5 mmol), and trimethylacetonitrile (0.334 g, 2.0 mmol) and methanol (5 mL) were used to prepare trimethylacetamidoxime (0.35 g, 100%) as described above.

Trimethylacetamidoxime (0.35 g, assumed 2.0 mmol), sodium hydride (60% dispersion in oil, 0.090 g, 2.2 mmol), benzyl 1-(4-methylpiperazin-1-yl)naphthalene-7-carboxylate (0.360 g, 1.0 mmol), and anhydrous tetrahydrofuran (15 mL total) were used to form the title compound as described above. Chromatographic purification using elution with ethyl acetate/methanol/triethylamine [40:1:1] afforded the title compound (0.168 g, 0.48 mmol, 48%) as a pile yellow foam: $^1$H NMR (CDCl$_3$) δ 9.00 (br s, 1H), 8.16 (dd, J=1.6 and 8.6Hz, 1H), 7.94 (d, J=8.6 Hz, 1H), 7.59–7.49 (m, 2H), 7.18 (dd, J=1.1 and 7.2Hz, 1H), 3.23 (br m, 4H), 2.84 (br m, 4H), 2.51 (s, 3H), 1.49 (s, 9H); LRMS (m/z, relative intensity) 351 (18), 350 (M$^+$, 100), 335 (10), 293 (29), 182 (29), 71 (50), 70 (46); HRMS calculated for C$_{21}$H$_{26}$N$_4$O 350.2101, found 350.2111. Anal. calculated for C$_{21}$H$_{26}$N$_4$O.H$_2$O: C, 68.45; H, 7.66; N, 15.20. Found: 68.14; H, 7.32; N, 14.91.

I. 7-(3-(3-Chlorophenylmethyl)-1,2,4-oxadiaz-5-y))-1-(4-methylpiperazin-1-yl)naphthalene Sodium (0.120 g, 5.2 mol), hydroxylamine hydrochloride (0.35 g, 5.0 mmol), and (3-chlorophenyl)acetonitrile (0.303 g, 2.0 mmol) and methanol (5 mL) were used to prepare (3-chlorophenyl)acetamidoxime (0.42 g, >100%) as described above.

(3-Chlorophenyl)acetamidoxime (0.42 g, assumed 2.0 mmol), sodium hydride (60% dispersion in oil, 0.093 g, 2.3 mmol), benzyl 1-(4-methylpiperazin-1-yl)naphthalene-7- carboxylate (0.360 g, 1.00 mmol), and anhydrous tetrahydrofuran (12 mL total) were to used form the title compound as described above. Chromatographic purification using elution with 10% methanol in ethyl acetate afforded the title compound (0.105 g, 0.25 mmol, 25%) as a pale yellow powder: $^{13}$C NMR (CDCl$_3$) δ 176.4, 169.6, 150.9, 137.5, 136.6, 134.5, 129.9, 129.5, 129.3, 128.7, 128.3, 127.4, 127.3, 125.2, 123.9, 123.2, 120.7, 116.0, 55.5, 53.2, 46.1, 32.1; LRMS (m/z, relative intensity) 420 ([M+with $^{37}$Cl], 29), 419 (32), 418 (M$^+$ with $^{35}$Cl], 100), 403 (14), 350 (53), 293 (28), 182 (39), 154 (39), 71 (95), 70 (63); HRMS calculated for C$_{24}$H$_{23}$ClN$_4$O: 418.1555, found 418.1583. Anal. calculated for C$_{24}$H$_{23}$ClN$_4$O.0.5 H$_2$O: C, 67.36; H, 5.65; N, 13.09. Found: C, 67.28; H, 5.54; N, 12.95.

J. 7-(3-Phenylpropyl-1,2,4-oxadiaz-5-yl)-1-(4-methylpiperazin-1-yl)naphthalene

Sodium (0.235 g, 10.2 mol), hydroxylamine hydrochloride (0.70 g, 10.1 mmol), and 4-phenylbutyronitrile (0.58 g, 4.0 mmol) and methanol (6 mL) were used to prepare 4-phenylbutyroamidoxime (0.79 g, >100%) as described above.

4-Phenylbutyroacetamidoxime (0.79 g, assumed 4.0 mmol), sodium hydride (60% dispersion in oil, 0.210 g, 5.2 mmol), benzyl 1-(4-methylpiperazin-1-yl)naphthalene-7-carboxylate (0.720 g, 2.00 mmol), and anhydrous tetrahydrofuran (20 mL total) were to used form the title compound as described above. Chromatographic purification using elution with 4–10% methanol gradient in ethyl acetate afforded the title compound (0.363 g, 0.88 mmol, 44%) as a pale yellow amorphous solid: $^1$H NMR (acetone-d$_6$) δ 9.01 (br s, 1H), 8.11 (dd, J=8.6 and 1.7 Hz, 1H), 8.04 (d, J=8.5 Hz, 1H), 7.66 (d, J=8.2 Hz, 1H), 7.56 (t, J=8.2 Hz, 1H), 7.32–7.15 (m, 6H), 3.12 (br m, 4H), 2.83 (t, J=7.4 Hz, 2H), 2.77 (t, J=7.4 Hz, 2H), 2.70 (br m, 4H), 2.35 (s, 3H), 2.18–2.08 (m, 2H); $^{13}$C NMR (CDCl$_3$) δ 176.3, 171.9, 151.8, 142.4, 137.4, 130.4, 129.6, 129.3, 129.1, 129.0, 126.6, 125.4, 124.4, 123.9, 121.6, 116.8, 56.1, 53.9, 46.2, 35.5, 25.9; FAB LRMS (m/z, relative intensity) 413 (MH$^+$, 100).

EXAMPLE 53

General Procedure for the Aminolysis of 1-(4-Methylpiperazin-1-yl)naphthalene-7-carboxylic Acid To a stirred solution of 1-(4-methylpiperazin-1-yl)naphthalene-7-carboxylic acid (0.270 g, 1.00 mmol) in anhydrous tetrahydrofuran (5 mL) at room temperature was added carbonyl diimidazole (0.178 mg, 1.10 mmol, 1.1 eq) directly as a solid. The resulting reaction solution was stirred at room temperature under nitrogen for 3 hours. The appropriate amine (1.1 mmol, 1.1 eq) was then added, and the resulting reaction solution was stirred at room temperature under nitrogen for 16 hours. A saturated solution of sodium hydrogen carbonate was added, and the resulting aqueous mixture was extracted with ethyl acetate (2×25 mL). The organic extracts were combined, dried (MgSO$_4$), and evaporated under reduced pressure. Column chromatography of the residue using silica gel (approximately 50 g) and an appropriate solvent system afforded the corresponding 1-(4-methylpiperazin-1-yl)naphthalene-7-carboxamide.

Using this procedure, the following compounds were prepared:

A. N-(2-(Indol-3-yl)ethyl)-1-(4-methylpiperazin-1-yl)naphthalene-7-carboxamide

Tryptamine was the amine used. Chromatography using elution with 20% methanol in ethyl acetate afforded the title compound (63%) as a white foam: R$_f$=0.20 [20% methanol in ethyl acetate]; $^{13}$C NMR (acetone-d$_6$) δ 167.9, 151.7, 137.7, 136.8, 132.7, 129.2, 128.9, 128.6, 128.3, 124.6, 124.3, 123.6, 123.3, 122.0, 119.3, 119.3, 116.0, 113.4, 112.1, 56.0, 53.8, 46.3, 41.5, 26.3; LRMS (m/z, relative intensity) 412 (M$^+$, 100), 269 (41), 143 (60), 130 (36), 71 (43), 70 (30); HRMS calculated for C$_{26}$H$_{29}$N$_4$O 412.2229, found 412.2305.

B. 1-(4-Methylpiperazin-1-yl)naphthalene-7-carboxamide

Ammonia was the amine used. Extraction of the reaction led directly to the title compound (35%) as a white foam: $^1$H NMR (CDCl$_3$) δ 8.71 (br s, 1H), 7.89 (d, J=8.5 Hz, 1H), 7.85 (dd, J=1.6 and 8.5 Hz, 1H), 7.59 (br d, J=8.1 Hz, 1H), 7.51 (t, J=7.3 Hz, 1H), 7.17 (d, J=1.1 and 7.2 Hz, 1H), 6.4–5.8 (br, 2H), 3.17 (br m, 4H), 2.76 (br m, 4H), 2.45 (s, 3H); $^{13}$C NMR (CDCl$_3$) δ 170.0, 150.8, 136.4, 130.1, 129.0, 128.2, 128.0, 123.8, 123.2, 115.7, 55.5, 53.2, 46.1; HRMS calculated for C$_{16}$H$_{19}$N$_3$O 269.1530, found 269.1542.

C. N-(4-Pyridylmethyl)-1-(4-methylpiperazin-1-yl)naphthalene-7-carboxamide 4-(Aminomethyl)pyridine was the amine used. Chromatography using elution with methylene chloride/methanol/ammonium hydroxide [10:4:0.4] afforded the title compound as an imidazoyl salt. This material was dissolved in methylene chloride (25 mL), and this solution was extracted with a solution of sodium carbonate (1 M, 2×20 mL). The ethyl acetate layer was dried (K$_2$CO$_3$) and evaporated under reduced pressure to afford the title compound (35%) as a pale yellow foam: LRMS (m/z, relative intensity) 360 (M$^+$, 50), 345 (46), 317 (100), 290 (27), 225 (27), 154 (35), 71 (66), 70 (48); HRMS calculated for C$_{22}$H$_{24}$N$_4$O 360.1945, found 360.1932. Anal. calcd for C$_{22}$H$_{24}$N$_4$O.H$_2$O: C, 69.82; H, 6.92; N, 14.80. Found: C, 69.82; H, 6.91; N, 14.53.

D. N-(3-Pyridylmethyl)-1-(4-methylpiperazin-1-yl)naphthalene-7-carboxamide 3-(Aminomethyl)pyridine was the amine used. Chromatography using elution with methylene chloride/methanol/ammonium hydroxide [20:1:0.1] afforded the title compound as an imidazoyl salt. This material was dissolved in methylene chloride (25 mL), and this solution was extracted with a solution of sodium carbonate (1 M, 2×20 mL). The ethyl acetate layer was dried (K$_2$CO$_3$) and evaporated under reduced pressure to afford the title compound (17%) as a white amorphous solid: $^{13}$C NMR (CD$_3$OD) δ 170.7, 160.7, 151.9, 149.2, 148.6, 137.6, 137.2, 137.0, 132.0, 130.0, 129.5, 129.2, 125.2, 125.2, 124.4, 116.9, 56.4, 53.8, 46.2, 42.2; LRMS (m/z, relative intensity) 360 (M$^+$, 36), 345 (43), 317 (100), 290 (30), 242 (30), 208 (35), 71 (75); HRMS calculated for C$_{22}$H$_{24}$N$_4$O 360.1945, found 360.1946.

E. N-(2-Pyridylmethyl)1-(4-methylpiperazin-1-yl)naphthalene-7-carboxamide 2-(Aminomethyl)pyridine was the amine used. Chromatography using elution with methylene chloride/methanol/ammonium hydroxide [9:1:0.1] afforded the title compound as an imidazoyl salt. This material was dissolved in methylene chloride (25 mL), and this solution was extracted with a solution of sodium carbonate (1 M, 2×20 mL). The ethyl acetate layer was dried (K$_2$CO$_3$) and evaporated under reduced pressure to afford the title compound (19%) as a pale yellow oil: $^{13}$C NMR (CD$_3$OD) δ 170.7, 159.5, 151.9, 149.8, 149.6, 138.9, 137.8, 132.1, 130.0, 129.5, 129.1, 125.2, 124.4, 124.0, 122.7, 116.9, 56.4, 53.8, 46.2, 46.0: LRMS (m/z, relative intensity) 360 (M$^+$, 100), 345 (71), 317 (38), 290 (48), 182 (64), 71 (89); HRMS calculated for C$_{22}$H$_{24}$N$_4$O 360.1945, found 360.1932.

F. N-(4-Pyridylethyl)-1-(4-methylpiperazin-1-yl) naphthalene-7-carboxamide 2-(2-Aminoethyl)pyridine was the amine used. Chromatography using elution with 20% methanol in ethyl acetate afforded the title compound as an imidazoyl salt. This material was dissolved in methylene chloride (25 mL), and this solution was extracted with a solution of sodium carbonate (1 M, 2×20 mL). The ethyl acetate layer was dried ($K_2CO_3$) and evaporated under reduced pressure to afford the title compound (54%) as a clear, pale brown oil: $R_f$=0.15 in 20% methanol in ethyl acetate; LRMS (m/z, relative intensity) 374 ($M^+$, 50), 359 (100), 331 (34), 304 (63), 208 (43), 182 (73), 149 (83); HRMS calculated for $C_{23}H_{26}N_4O$ 374.2106, found 374.2111.

EXAMPLE 54

N-(5-(1,1,-Dimethylethyl)-1,2,4-oxadiaz-3-ylmethyl)-1-(4-methylpiperazin-1-yl)naphthalene-7-carboxamide To solution of 1-(4-methylpiperazin-1-yl)naphthalene-7-carboxamide (0.100 g, 0.37 mmol) in anhydrous tetrahydrofuran (5 mL) at −10° C. was added lithium diisopropylamide (1.5 M in tetrahydrofuran, 0.30 mL, 0.45 mmol, 1.2 equivalents), and the resulting reaction solution was allowed to warm to room temperature. Then, 3-(chloromethyl)-5-(1, 1-dimethylethyl)-1,2,4-oxadiazole (0.078 g, 0.45 mmol, 1.2 eq) was added, and the resulting reaction solution was heated at reflux under nitrogen for 22 hours. A saturated solution of sodium hydrogen carbonate was then added, and the resulting aqueous mixture was extracted with ethyl acetate (2×20 mL). The organic extracts were combined, dried ($MgSO_4$), and evaporated under reduced pressure. Column chromatography of the residue using silica gel (approximately 25 g) and elution with 5% triethylamine in ethyl acetate afforded the title compound (0.035 g, 0.09 mmol, 23%) as a yellow oil: $R_f$=0.40 in ethyl acetate/methanol/triethylamine [8:1:1]; $^1$H NMR ($CDCl_3$) δ 8.88 (br s, 1H), 7.84 (s, 2H), 7.54 (d, J=8.0 Hz, 1H), 7.46 (br t, J=8.2 Hz, 1H), 7.12 (dd, J=1.0 and 7.3 Hz), 6.98 (br t, NH), 4.83 (d, J=5.4 Hz, 2H), 3.13 (br m, 4H), 2.73 (br m, 4H), 2.40 (s, 3H), 1.43 (s, 9H); LRMS (m/z, relative intensity) 407 ($M^+$, 46), 392 (20), 182 (45), 151 (57), 113 (54), 71 (100), 70 (34); HRMS calculated for $C_{23}H_{29}N_5O_2$ 407.2315, found 407.2310.

PREPARATION 1

8-(4-methylpiperazin-1-yl)naphthalen-2-ol

To a stirring solution of 8-amino-2-naphthol (3.28 g, 20 mmol, Aldrich Chem, Co.) in 100 mL of acetonitrile was added sodium bicarbonate (7.42 g, 88 mmol), sodium iodide (6.72 g, 44 mmol) and mechlorethamine hydrochloride (4.32 g, 22 mmol). Under nitrogen, the reaction was heated to reflux and stirred for another 2 hr. The reaction mixture was then allowed to cool to room temperature and was stirred overnight. A thin layer chromatography (tlc) using methylene chloride:methanol:conc. ammonium hydroxide (90:10:1) showed the more polar product ($R_f$ 0.25) with only a trace of the starting naphthol. Silica gel (4.5 g) was added and the reaction mixture was concentrated in vacuo to a dry purple solid. This was added to a column of silica gel (ca. 400 g) and eluted with 2 L volumes of $CH_2Cl_2$, $CH_2Cl_2$:$CH_3OH$ (40:1), $CH_2Cl_2$:$CH_3OH$:conc. $NH_4OH$ (20:1:0.1) and finally 4 L of $CH_2Cl_2$:$CH_3OH$:conc. $NH_4OH$ (10:1:0.1). The appropriate fractions were combined to yield a purple-black solid, 5.26 g, mp 184–185° C.

$^1$H NMR ($CD_3OD$) δ 2.40 (s, 3H), 2.72 (bs, 4H), 3.05 (bs, 4H), 7.05 (d, 2H), 7.18 (t, 1H), 7.45(m, 2H), 7.67 (d, 1H). Mass spectrum: m/e 242 ($M^+$).

PREPARATION 2

Trifluoromethanesulfonic Acid 8-(4-methylpiperazin-1-yl)naphthalen-2-yl Ester

To a stirred suspension of 8-(4-methylpiperazin-1-yl) naphthalen-2-ol (5.0 g, 20 mmol) in anhydrous methylene chloride (50 mL), cooled to −78° C. was added triethylamine (20 mL) followed by trifluoromethanesulfonic anhydride (3.9 mL). After a further hr at −78° C., the cooling bath was removed, silica gel (4.5 g) was added and the solvent was removed in vacuo. The resulting slurry was added to a column of 400 g of silica gel and the product was eluted with an ethyl acetate:methanol gradient (100:0 to 80:20). The product fractions were concentrated in vacuo to provide the title product, 4.32 g.

PREPARATION 3

8-(4-Methylpiperazin-1-yl)naphthalene-2-carboxylic Acid Benzyl Ester

A mixture of the preceding compound (34 g, 90.8 mmol, 1.0 equiv.), benzyl alcohol (170 mL), bis(triphenylphosphine)palladium(II) chloride (6.2 g, 8.8 mmol, 0.1 equiv.), lithium chloride (0.44 g, 10.5 mmol, 0.1 equiv.) and triethylamine (32 mL) was shaken under an atmosphere of carbon monoxide (50 psi) at 70° C. for 6.5 hours. The resulting reaction solution was directly filtered through silica gel (2 kg, pre-wet with ethyl acetate) and eluted with ethyl acetate (8 L) followed by 5% methanol in ethyl acetate to afford the title compound (28.04 g, 77.8 mmol, 86%) as a pale brown foam. $^1$H NMR (acetone-$D_6$) δ 9.00 (d, J=0.7 Hz, 1 H), 8.04 (dd, J=8.6 and 1.7 Hz, 1 H), 7.96 (d, J=8.6 Hz, 1 H), 7.66 (d, J=8.2 Hz, 1 H), 7.59–7.53 (m, 3H), 7.47–7.36 (m, 3H), 7.22 (dd, J=7.3 and 1.1 Hz, 1H), 5.43 (s, 2H), 3.20 (br m, 4H), 2.91 (br m, 4H), 2.54 (s, 3H). LRMS (m/e, relative intensity) 361 ($M^+$, 29). HRMS calculated for $C_{23}H_{24}N_2O_2$: 360.1839. Found: 360.1832.

PREPARATION 4

8-(4-Methylpiperazin-1-yl)naphthalene-2-carboxylic Acid

A mixture of 8-(4-methylpiperazin-1-yl)naphthalene-2-carboxylic acid benzyl ester (0.20 g, 5.55 mmol) and Pd(OH) on carbon (0.11 g) in 2 mL of ethanol was hydrogenated on a Parr shaker apparatus at 50 psi for 5 hr. After diluting with ethanol and filtering through diatomaceous earth, the solvent was removed in vacuo to yield the title product as a foam, 138 mg.

PREPARATION 5

1-(1-Methylpiperidin-4-yl)-7-trifluoromethanesulfonyloxynaphthalene

In two side by side reactions, 8-bromo-2-tetralone (7.0 g, 31.25 mmol) and N-bromosuccinimide (5.84 g, 32.8 mmol) were combined in carbon tetrachloride and refluxed 45 min. The reactions were cooled, filtered through diatomaceous earth (Celite™), and combined for workup. The organic solution was washed with saturated aqueous sodium bicarbonate and brine followed by drying through phase separating filter paper (1 PS) and concentrated to give 14.44 g (104% crude) of 8-bromo-2-naphthol as a brown solid which was suitable for further reaction. A sample dissolved in methylene chloride and treated with activated carbon, concentrated, and triturated with hexane had: mp 96–100° C.; $^1$HNMR (250 MHz, CDCl$_3$) δ 7.79–7.73 (m, 3 H), 7.56 (d, J=4.5 Hz, 1 H), 7.22–7.14 (m, 3 H). HRMS m/e calculated for C$_{10}$H$_7$BrO: 221.9680. Observed m/e: 221.9664.

In two side by side reactions, 8-bromo-2-naphthol (7.22 g, 32.5 mmol) was dissolved in tetrahydrofuran (200 mL) and chilled to −78° C. Butyl lithium (31.2 mL, 74.8 mmol) was rapidly added (1–2 min) and the solution was stirred for 12 min. 1-Methyl-4-piperidone (4.22 mL, 34.2 mmol, dissolved in 10 mL of tetrahydrofuran) was added dropwise to the solution with a 10 mL, tetrahydrofuran rinse. The reaction was stirred at −78° C. for an additional 30 min, then allowed to warm to room temperature. The reactions were combined and concentrated directly onto silica gel and flash chromatographed (3.5×4 inches of silica gel, packed with ethyl acetate). Elution proceeded as follows: ethyl acetate, 500 mL, nil; 2% methanol/1% triethylamine/ethyl acetate, 1000 mL, nil; 4% methanol/2% triethylamine/ethyl acetate, 2000 mL, nil; 6% methanol/3% triethylamine/ethyl acetate, 3000 mL, 7.64 g of pure 1-(1-methyl-4-hydroxypiperidin-4-yl)-7-hydroxynaphthalene. Continued elution with 8% methanol/4% triethylamine/ethyl acetate, 2000 mL, 4.32 g of additional product which was significantly contaminated with a triethylamine derived impurity, possibly a salt. A sample of the pure product recrystallized from dioxane as a ⅓ methanolate had: mp 206–208° C. (dec.); $^1$HNMR (250 MHz, DMSO$_{d6}$) δ 9.63 (s, 1 H), 8.20 (d, J=2 Hz, 1 H), 7.73 (d, J=9 Hz, 1 H), 7.65 (d, J=8 Hz, 1 H), 7.47 (d, J=6.5 Hz, 1 H), 7.18 (t, J=7.5 Hz, 1 H), 7.02 (dd, J=2.5, 9 Hz, 1 H), 4.96 (s, 1 H), 2.70–2.46 (m, 4 H partially obscured by the NMR solvent), 2.22 (s, 3 H), 2.21–2.00 (m, 4 H). There were also two singlets at δ 5.76 and 3.56 which integrated for the ⅓ methanolate. Analysis calculated for C$_{16}$H$_{19}$NO$_2$.0.33 CH$_4$O: C, 73.29; H, 7.53; N, 5.23. Found: C, 73.61; H, 7.62; N, 5.32.

A mixture of 1-(1-methyl-4-hydroxypiperidin-4-yl)-7-hydroxynaphthalene (7.64 g, 29.7 mmol) and p-toluenesulfonic acid (6.78 g, 35.7 mmol) in dioxane (250 mL) was refluxed overnight. The solvent was removed at reduced pressure and the residue was taken up in methylene chloride. The naphthol product was extracted from this organic phase with 1 N sodium hydroxide, 4 N sodium hydroxide and then 1 N sodium hydroxide. The combined basic aqueous phase was neutralized to pH 8 with saturated aqueous sodium bicarbonate and extracted with warm chloroform (3×, two phase mixture vigorously magnetically stirred while heat was applied by means of a hot plate.) The combined organic phase (still warm) was washed with brine, dried over calcium sulfate and concentrated to afford 5.01 g (83% for this step) of 1-(1-methyl-1,2,3,6-tetrahydropyrid-4-yl)-7-hydroxynaphthalene as a tan solid. A sample recrystallized from ethyl acetate had: mp 182.5–184° C.; $^1$HNMR (250 MHz, CDCl$_3$) δ 9.15 (s, 1 H), 7.98 (d, J=2.5 Hz, 1 H), 7.69 (d, J=9 Hz, 1H), 7.65 (d, J=8 Hz, 1 H), 7.25–7.12 (m, 2 H), 7.03 (dd, J=2.5, 9 Hz, 1 H), 5.70 (sym m, 1 H), 3.32 (sym m, 2 H), 2.92 (t, J=6 Hz, 2 H), 2.70–2.60 (m, 2 H), 2.66 (s, 3 H). Analysis calculated for C$_{16}$H$_{17}$NO.0.25 H$_2$O: C, 78.82; H, 7.23; N, 5.74. Found: C, 78.81; H, 7.21; N, 5.83.

The 4.32 g of impure 1-(1-methyl-4-hydroxypiperidin-4-yl)-7-hydroxynaphthalene was subjected to the identical dehydration conditions above and 1.13 g of crude product was obtained. Recrystallization from ethyl acetate gave 0.855 g of 1-(1-methyl-1,2,3,6-tetrahydropyrid-4-yl)-7-hydroxynaphthalene as white crystals. Thus a total of 5.865 g was obtained for a total yield of 39% for the above two steps.

A mixture of 1-(1-methyl-1,2,3,6-tetrahydropyrid-4-yl)-7-hydroxynaphthalene (5.865 g, 24.54 mmol), 20% palladium on carbon (5.9 g), methanol (210 mL), and acetic acid (30 mL) was hydrogenated for 6.5 h (initial pressure—40 psi). The mixture was filtered through celite and the pad was rinsed well with methanol. The solvent was removed at reduced pressure and the residue was neutralized with saturated aqueous sodium bicarbonate. This mixture was extracted with hot chloroform (3×) and with warm methylene chloride (1×). The combined organic phase (still hot) was washed with brine (prewarmed to the same temperature as the chloroform solution, approximately 60° C.), dried over calcium sulfate and concentrated to afford 2.0 9 of brown solid product. The aqueous bicarbonate phase above was concentrated to dryness. The residue was extracted with hot chloroform and filtered. The hot extraction process was repeated successively with methylene chloride, ethanol and once again with chloroform. The combined solutions were concentrated to afford an additional 3.26 g of brown solid. In this fashion, 5.26 g (89%) of 1-(1-methylpiperidin-4-yl)-7-hydroxynaphthalene was obtained. The material was suitable for use in the next step without purification. A sample recrystallized from methanol had: mp 196.5–199° C.; $^1$H NMR (250 MHz, CDCl$_3$) δ 7.76 (d, J=9 Hz, 1 H), 7.62 (d, J=8 Hz, 1 H), 7.40 (d, J=2 Hz, 1 H), 7.26 (sym m, partially obscured by the NMR solvent, 2 H), 7.09 (dd, J=2.5, 9 Hz, 1 H), 3.26–3.08 (m, 3 H), 2.42 (s, 3 H), 2.35–2.20 (m, 2 H), 2.16–1.92 (m, 4 H). Analysis calculated for C$_{16}$H$_{19}$NO: C, 79.63; H, 7.94; N, 5.80. Found: C, 79.22; H, 8.18; N, 5.83.

A solution of 1-(1-methylpiperidin-4-yl)-7-hydroxynaphthalene (3.47 g, 14.4 mmol) in methylene chloride (150 mL) was treated with triethylamine (9.03 mL, 64.8 mmol) and chilled to −78° C. Triflic anhydride (3.03 mL, 18.0 mmol) was added dropwise to the reaction with a 10 mL methylene chloride rinse. The reaction was allowed to warm to room temperature and stir overnight. The reaction was concentrated with a nitrogen stream and the residue was partitioned between methylene chloride and saturated aqueous sodium bicarbonate. The phases were separated and the organic phase was washed with brine, dried over calcium sulfate and concentrated. The residue was flash chromatographed on silica gel (2×3 inches packed in 75% ethyl acetate/hexane). Elution proceeded as follows: 75% ethyl acetate/hexane, 500 mL, nil; ethyl acetate, 600 mL, nil; 2% methanol/1% triethylamine/ethyl acetate, 600 mL, nil; 5% methanol/2% triethylamine/ethyl acetate, 600 mL, 2.74 g (51%) of 1-(1-methylpiperidin4-yl)-7-trifluoromethanesulfonyloxynaphthalene as a light brown crystalline solid suitable for further reaction. A sample recrystallized from ethyl acetate I hexane had: mp 144–146° C.; $^1$H NMR (250 MHz, CDCl$_3$) δ 7.96–7.91 (m, 2 H), 7.76 (dd, J=2.5, 7 Hz, 1 H), 7.58–7.51 (m, 2 H), 7.36 (dd, J=2.5, 9 Hz, 1 H), 3.25–3.12 (m, 3 H), 2.48 (s, 3 H), 2.37 (sym m, 2 H), 2.19–1.95 (m, 4 H). HRMS mile calculated for C$_{17}$H$_{18}$F$_3$NO$_3$S: 373.0954. Observed m/e: 373.0898.

Synthesis of intermediates used in the above examples are described in the preparations below.

PREPARATION 6

7-hydroxy-1-(4-methyl-1-piperazinyl)-3,4-dihydronaphthalene

7-Hydroxy-α-tetralone (1.0 g, 6.17 mmol, Corey and Estreicher, Tetrahedron Lett., 1981, 22, 603) and 1-methylpiperazine (2.2 mL, 19.83 mmol) were dissolved in dry THF (90 mL) and chilled to 0° C. Titanium tetrachloride (0.91 mL, 8.3 mmol) was allowed to run down the side of the reaction vessel into the reaction via syringe to give a vigorous reaction which caused the solution to turn orange-red. The mixture was allowed to warm to ambient temperature and stir 1.5 hours. A 2:1 mixture of water and concentrated ammonium hydroxide (90 mL) was added and the mixture was extracted with ethyl acetate. The organic phase was dried over calcium sulfate and concentrated to give 1.48 g of crude enamine which was used immediately without characterization. (This enamine was not stable to chromatography but did show a characteristic signal in the $^1$H NMR for the enamine vinyl proton at 5.28 ppm with a 4.7 Hz coupling constant).

PREPARATION 7

7-Hydroxy-1-(4-methyl-1-piperazinyl)-naphthalene

10% Palladium on carbon (1.16 g) and 7-hydroxy-1-(4-methyl-1-piperazinyl)-2,3-dihydronaphthalene (1.48 g, 6.06 mmol) were slurried in toluene (100 mL) and refluxed 16.5 h. The mixture was cooled, filtered, and concentrated. The product was purified by flash chromatography on silica gel (1×6 inches). Elution with 50% ethyl acetate/hexane followed by 100% ethyl acetate gave 0.51 g (34%) of the title product as a light pink foam. A sample was recrystallized from ether to give a cream colored solid for analysis: mp 184–185° C. Analysis calculated for $C_{15}H_{18}N_2O$: C, 74.35; H, 7.49; N, 11.56. Found: C, 74.05; H, 7.03; N, 11.42.

PREPARATION 8

7-Trimethylstannyl-1-(4-methyl-1-piperazinyl)-naphthalene 7-trifluoromethylsulfonyloxy-1-(4-methyl-1-piperazinyl)-naphthalene (2.0 g, 5.34 mmol), hexamethylditin (1.92 g, 5.86 mmol), lithium chloride (0.68 g. 16 mmol), tetrakis (triphenylphosphine) palladium (0.24 g, 0.21 mmol) and butylated hydroxytoluene (a few crystals, antioxidant) were combined in dry dioxane (50 mL) and refluxed 45 minutes. The mixture was cooled and quenched with saturated ammonium chloride (50 mL). The mixture was extracted with ether (2×) and the combined organic phase was washed with brine, dried over magnesium sulfate, and concentrated to a brown oil. Flash chromatography on silica gel (2×4 inches) with 50% ethyl acetate/hexane elution gave 0.77 g (37%) of the title product as a light brown oil which slowly solidified. The product was suitable for use in subsequent reactions but was not analytically pure: $^1$H NMR δ 8.36 (s with Sn coupling, 1H), 7.80 (d, J=8 Hz, 1H), 7.61–7.51 (m, 2H), 7.40 (t, J=8 Hz, 1H), 7.09 (dd, J=1, 7.5 Hz, 1H), 3.2 (br s, 4H), 2.75 (br s, 4H), 2.46 (s, 3H), 0.39 (s with Sn coupling of 55.0 and 52.5 Hz, 9H).

PREPARATION 9

5-Chloromethyl-3-phenyl-1,2,4-oxadiazole

A solution of benzamidoxime (0.77 g, 5.68 mmol) and triethylamine (0.95 mL, 0.82 mmol) in toluene (10 mL) was treated with 0.45 mL (5.65 mmol) of chloroacetyl chloride at room temperature for 30 min., refluxed for 18 hours, cooled to room temperature and concentrated in vacuo. The residue was diluted with water, and extracted with ethyl acetate. The organic extracts were then washed with water and dried with $MgSO_4$. Concentration in vacuo gave an oil which was chromatographed on silica gel using ethyl acetate, hexanes (1.9), giving 0.24 of the title compound as a light yellow oil which solidified on standing. $^1$H NMR (250 MHz, $CDCl_3$) δ 8.1 (m, 2H), 7.5 (m, 3H), 4.8 (s, 2H).

In the same manner, the following analogs were prepared:

5-Chloromethyl-3-(2-methoxyphenyl-1,2,4-oxadiazole white semi-solid, $^1$H NMR (250 MHz, $CDCl_3$) δ 8.0 (dd, 2H), 7.5 (m, 1H), 7.0 (m, 2H), 4.8 (s, 2H), 4.0 (s, 3H).

5-Chloromethyl-3-(4-methoxyphenyl)-1,2,4oxadiazole, semi-solid, $^1$H NMR (250 MHz, $CDCl_3$) δ 8.0 (d, 2H), 7.0 (d, 2H), 4.8 (s, 2H), 4.0 (s, 3H); mass spectrum m/e 224 ($M^+$)

5-Chloromethyl-3-(4-chlorophenyl)-1,2,4-oxadiazole, semi-solid, $^1$H NMR (250 MHz, $CDCl_3$) δ 8.0 (d, 2H), 7.5 (d, 2H), 4.8 (s, 2H); mass spectrum: m/e 228 ($M^+$).

PREPARATION 10

3-Chloromethyl-5-(4-chlorophenyl)-1,2,4-oxadiazole

A solution of 2-chloroacetamidoxime (0.5 g) and sodium bicarbonate (0.78 g) in 10 mL of anhydrous acetone was treated with 4-chlorobenzoyl chloride (0.58 mL) at room temperature for 2 hours, concentrated in vacuo, dissolved in water and extracted with ethyl acetate. The organic layers were combined, dried with $MgSO_4$ and concentrated to a semi-solid. This material was redissolved in toluene (50 mL). refluxed under nitrogen for 15 hours, cooled and absorbed on to silica gel. Chromatography using ethyl acetate:hexane (1:9) gave the pure title product as a light yellow solid, mp 79–80° C. Mass spectrum m/e: 228 ($M^+$), $^1$H NMR (250 MHz, $CDCl_3$) δ 8.1 (d, 2H), 7.5 (d, 2H), 4.7 (s, 2H).

PREPARATION 11

5-Bromo-8-(4-methylpiperazin-1-yl)naphthalene-2-carboxylic Acid 4-chloro-benzylamide To a solution of 8-(4-methylpiperazin-1-yl)-naphthalene-2-carboxylic acid 4-chlorobenzylamide (0.100 g, 0.256 mmol) and sodium bicarbonate (0.106 g, 1.26 mmol) in 2 mL of methanol was added bromine (26 μL, 0.50 mmol) in 0.5 mL of dichloromethane. After stirring for 30 min at room temperature the reaction mixture was evaporated in vacuo and the residue was treated with water and extracted with dichloromethane. The organic extracts were dried with $MgSO_4$ and concentrated to a yellow oil. Chromatography on silica gel using methanol/conc. ammonium hydroxide/dichloromethane (2.0/0.2/97.9) gave 0.040 g (33%) of the title product as an oil which slowly solidified, mp 103° C. (dec). Mass spectrum: m/e 475 (M+1), 395 ($M^+$—Br), $^1$H NMR ($CDCl_3$) δ 8.6 (d, 1H), 8.3 (d, 1H), 7.8 (dd, 1H), 7.7 (d, 1H, 7.3 (s, 4H), 7.0 (d, 1H), 6.8 (t, 1H), 4.7 (d, 2H), 3.1 (bs, 4H), 2.7 (bs, 4H), 2.5 (s, 3H).

In the same manner, 8-(4methylpiperazin-1-yl)-naphthalene-2-carboxylic acid 4-chloro-3-iodo-benzylamide was converted in 72% yield to 5-bromo-8-(4-methylpiperazin-1-yl)-naphthalene-2-carboxylic acid 4-chloro-3-iodo-benzylamide, mp 131° C. (dec). Mass spectrum: m/e 808,598. $^1$H NMR ($CDCl_3$) δ 8.7 (d, 1 H), 8.2 (d, 1H), 7.5 (m, 2H), 7.7 (d, 1H), 7.4 (d, 1H), 7.3 (dd, 1H), 7.0 (d, 1H), 6.7 (t, 1H), 4.7 (d, 2H), 3.2 (bs, 4H), 2.7 (bs, 4H), 2.5 (s, 3H).

We claim:

1. A compound of the formula

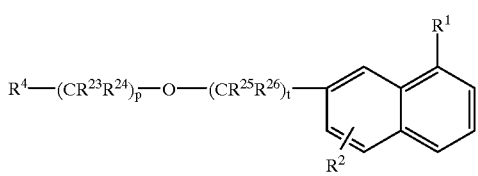

I wherein $R^1$ is

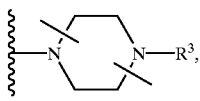

II e is 0, 1 or 2;
m is an integer from zero to six;
n is an integer from one to three;
p is an integer from one to six;
t is an integer from zero to three;
$R^2$ is a substituent on any of the carbon atoms of the naphthalene ring capable of forming an additional bond and each occurence of $R^2$ is independently selected from the group consisting of hydrogen, fluoro, chloro, bromo, iodo, —CN, —NO$_2$, (C$_1$–C$_6$)alkyl optionally substituted with from one to seven fluorine atoms, (C$_1$–C$_6$)alkoxy optionally substituted with from one to seven fluorine atoms, —(C$_1$–C$_6$)thioalkyl optionally substituted with from one to seven fluorine atoms, —OH, —NR$^{20}$R$^{21}$, —CONR$^{20}$R$^{21}$, and —CO$_2$R$^{20}$;
$R^3$ is hydrogen, (C$_1$–C$_{10}$)alkyl optionally substituted with from one to seven fluorine atoms, —(CH$_2$)$_m$-aryl, —(CH$_2$)$_m$—(C$_5$–C$_7$)cycloalkyl, —(CH$_2$)$_n$—R$^{27}$, —CO$_2$R$^{20}$, or (C$_1$–C$_6$)alkoxy optionally substituted with from one to seven fluorine atoms; wherein said aryl moeity of said –(CH$_2$)$_m$-aryl group may optionally be substituted with from one to three substituents independently selected from any of the substituents listed for $R^2$; and wherein said (C$_5$–C$_7$)cycloalkyl moiety of said —(CH$_2$)$_m$—(C$_5$–C$_7$)cycloalkyl group may optionally be substituted with from one to three substituents independently selected from any of the substituents listed for $R^2$;
$R^4$ is

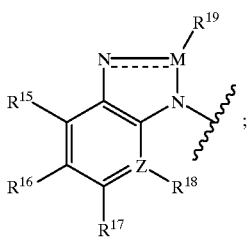

XVII $R^{15}$, $R^{16}$, $R^{17}$, and $R^{18}$ are each independently selected from hydrogen, bromo, chloro, fluoro, aryl, (C$_1$–C$_6$) alkyl optionally substituted with from one to seven fluorine atoms, (C$_1$–C$_5$)alkoxy optionally substituted with from one to seven fluorine atoms, (C$_1$–C$_5$) alkylthio optionally substituted with from one to seven fluorine atoms, formyl, —(C=O)R$^{20}$, —CN, —OR$^{20}$, —NR$^{20}$R$^{21}$, —NR$^{20}$SO$_2$R$^{22}$, —NR$^{20}$CO$_2$R$^{22}$, —N=C—N(CH$_3$)$_2$, —S(O)$_e$R$^{20}$, —SO$_2$NR$^{20}$R$^{21}$, —NO$_2$, aryl, (C$_1$–C$_6$)alkylaryl, —(C=O)OR$^{20}$, —(C=O)NR$^{20}$R$^{21}$, (C$_1$–C$_6$)alkyl, (C$_1$–C$_6$)alkenyl, and (C$_1$–C$_6$)alkynyl;

$R^{19}$ is hydrogen or (C$_1$–C$_3$)alkyl;

each occurence of $R^{20}$ and each occurence of $R^{21}$ is independently hydrogen, (C$_1$–C$_6$)alkyl, aryl, or (C$_1$–C$_6$)alkyl-aryl, or any occurence of $R^{20}$ and $R^{21}$, when attached to the same nitrogen atom, may form, together with the nitrogen to which they are attached, a (C$_4$–C$_7$)alkyl ring;

$R^{22}$ is (C$_1$–C$_6$)alkyl, aryl, or (C$_1$–C$_6$)alkylaryl;

Z is C or N, wherein $R^{18}$ is absent when Z is N;

M is C, N, or (C—O), wherein $R^{19}$ is absent when M is C=O;

$R^{23}$ and $R^{24}$ are independently selected from hydrogen, —(C$_1$–C$_6$)alkyl optionally substituted with from one to seven fluorine atoms, and when p is greater than 1 then each $R^{23}$ and $R^{24}$ is independently selected from any other $R^{23}$ or $R^{24}$;

$R^{25}$ and $R^{26}$ are independently selected from hydrogen, —(C$_1$–C$_6$)alkyl optionally substituted with from one to seven fluorine atoms, and when t is greater than 1 then each $R^{25}$ and $R^{26}$ is independently selected from any other $R^{25}$ or $R^{26}$;

$R^{27}$ is —OR$^{20}$, —C(=O)NR$^{20}$R$^{21}$, —C(=O)OR$^{20}$, CN, —NR$^{20}$C(=O)R$^{21}$, —O(C=O)R$^{20}$;

a broken line indicates the optional presence of a double bond; and the above aryl groups and the aryl moieties of the above alkylaryl groups are independently selected from phenyl, naphthyl, substituted naphthyl and substituted phenyl, wherein said substituted naphthyl and substituted phenyl may be substituted with one to three groups independently selected from (C$_1$ to C$_4$)alkyl optionally substituted with one to three fluorine atoms, halogen, hydroxy, cyano, carboxamido, nitro, and (C$_1$ to C$_4$)alkoxy optionally substituted with one to three fluorine atoms;

and the pharmaceutically acceptable salts thereof.

2. A compound according to claim 1, wherein $R^1$ is

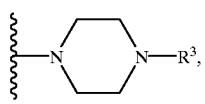

II p is 1; t is zero; and $R^2$, $R^{23}$ and $R^{24}$ are each hydrogen.

3. A pharmaceutical composition for treating a condition selected from hypertension, depression, generalized anxiety disorder, phobias, posttraumatic stress syndrome, avoidant personality disorder, sexual dysfunction, eating disorders, obesity, chemical dependencies, cluster headache, migraine, pain, Alzheimer's disease, obsessive compulsive disorder, panic disorder, memory disorders, Parkinson's diseases, endocrine disorders, vasospasm, gastrointestinal tract disorders and chronic paroxysmal hemicrania and headache associated with vascular disorders in a mammal, comprising an amount of a compound according to claim 1 effective in treating such condition and a pharmaceutically acceptable carrier.

* * * * *